United States Patent
Marion

(10) Patent No.: US 12,303,556 B2
(45) Date of Patent: *May 20, 2025

(54) PEPTIDES FOR TREATMENT AND PREVENTION OF DIABETES AND ASSOCIATED DISORDERS

(71) Applicants: UNIVERSITE DE STRASBOURG, Strasbourg (FR); INSERM (INSTITUT NATIONAL DE LA SANTÉ ET DE LA RECHERCHE MÉDICALE), Paris (FR)

(72) Inventor: Vincent Marion, Lipsheim (FR)

(73) Assignees: UNIVERSITE DE STRASBOURG, Strasbourg (FR); INSERM (INSTITUT NATIONAL DE LA SANTÉ ET DE LA RECHERCHE MÉDICALE), Paris (FR)

( * ) Notice: Subject to any disclaimer, the term of this patent is extended or adjusted under 35 U.S.C. 154(b) by 858 days.

This patent is subject to a terminal disclaimer.

(21) Appl. No.: 17/415,796

(22) PCT Filed: Dec. 20, 2019

(86) PCT No.: PCT/EP2019/086573
§ 371 (c)(1),
(2) Date: Jun. 18, 2021

(87) PCT Pub. No.: WO2020/127904
PCT Pub. Date: Jun. 25, 2020

(65) Prior Publication Data
US 2022/0133860 A1  May 5, 2022

(30) Foreign Application Priority Data
Dec. 21, 2018 (EP) .................................. 18306794

(51) Int. Cl.
*A61K 38/10* (2006.01)
*A61K 38/45* (2006.01)
*A61K 45/06* (2006.01)
*A61P 3/10* (2006.01)

(52) U.S. Cl.
CPC .............. *A61K 38/45* (2013.01); *A61K 45/06* (2013.01); *A61P 3/10* (2018.01)

(58) Field of Classification Search
None
See application file for complete search history.

(56) References Cited

U.S. PATENT DOCUMENTS

| 10,821,159 | B2 | 11/2020 | Marion et al. | |
| 11,332,503 | B2* | 5/2022 | Marion | A61K 38/28 |
| 11,530,241 | B2* | 12/2022 | Marion | C07K 14/00 |
| 2023/0340021 | A1* | 10/2023 | Marion | A61K 38/17 |

FOREIGN PATENT DOCUMENTS

| CN | 102 477 074 | 9/2013 | |
| WO | WO 00/18895 | 4/2000 | |
| WO | WO 2007/000770 | 1/2007 | |
| WO | WO 2015/114062 | 8/2015 | |
| WO | WO-2019002583 A1 * | 1/2019 | A61K 31/155 |

OTHER PUBLICATIONS

Gonzales, M. A., "Force fields and molecular dynamics simulations." Collection SFN (2011) 12 p. 169-200.*
Guo, Haiwei H. et al; "Protein tolerance to random amino acid changes." PNAS (2004) 101(25) p. 9205-9210.*
Yampolsky, Lev Y. et al.; "The exchangeability of amino acids in proteins." Genetics (2005) 170 p. 1459-1472.*
Uniprot variant map of human PKC, https://www.uniprot.org/uniprotkb/P17252/variant-viewer, downloaded Apr. 23, 2024.*
Lowe, Derek; "Not alphafold's fault." Blog "In the pipeline" entry of Sep. 7, 2022.*
Howes, Laura, "Deepmind ai predicts protein structure." C&EN, issue of Dec. 1, 2020.*
Martyn, J. A. Jeevendra et al., "Obesity induced insulin resistance and hyperglycemia: etiological factors and molecular mechanisms." Anesthesiology (2008) 109(1) p. 137-148.*
Brown, Sharon A et al., "Promoting weight loss in type ii diabetes." Diabetes Care (1996) 19(6) p. 613-624.*
Gruben, Nanda et al., "Nonalcoholic fatty liver disease: a main driver of insulin resistance or a dangerous liason." Biochim. Biophys. Acta (2014) 1842 p. 2329-2343.*
Written Opinion in International Application No. PCT/EP2019/086573, Apr. 8, 2020, pp. 1-7.

* cited by examiner

*Primary Examiner* — Fred H Reynolds
(74) *Attorney, Agent, or Firm* — SALIWANCHIK, LLOYD & EISENSCHENK

(57) ABSTRACT

The present invention relates to peptides for the treatment of diabetes and associated disorders.

10 Claims, 6 Drawing Sheets

Specification includes a Sequence Listing.

SEQUENCE LISTING

<160> NUMBER OF SEQ ID NOS: 57

<210> SEQ ID NO 1
<211> LENGTH: 672
<212> TYPE: PRT
<213> ORGANISM: Homo sapiens

<400> SEQUENCE: 1

```
Met Ala Asp Val Phe Pro Gly Asn Asp Ser Thr Ala Ser Gln Asp Val
1               5                   10                  15

Ala Asn Arg Phe Ala Arg Lys Gly Ala Leu Arg Gln Lys Asn Val His
            20                  25                  30

Glu Val Lys Asp His Lys Phe Ile Ala Arg Phe Phe Lys Gln Pro Thr
        35                  40                  45

Phe Cys Ser His Cys Thr Asp Phe Ile Trp Gly Phe Gly Lys Gln Gly
    50                  55                  60

Phe Gln Cys Gln Val Cys Cys Phe Val Val His Lys Arg Cys His Glu
65                  70                  75                  80

Phe Val Thr Phe Ser Cys Pro Gly Ala Asp Lys Gly Pro Asp Thr Asp
                85                  90                  95

Asp Pro Arg Ser Lys His Lys Phe Lys Ile His Thr Tyr Gly Ser Pro
            100                 105                 110

Thr Phe Cys Asp His Cys Gly Ser Leu Leu Tyr Gly Leu Ile His Gln
        115                 120                 125

Gly Met Lys Cys Asp Thr Cys Asp Met Asn Val His Lys Gln Cys Val
    130                 135                 140

Ile Asn Val Pro Ser Leu Cys Gly Met Asp His Thr Glu Lys Arg Gly
145                 150                 155                 160

Arg Ile Tyr Leu Lys Ala Glu Val Ala Asp Glu Lys Leu His Val Thr
                165                 170                 175

Val Arg Asp Ala Lys Asn Leu Ile Pro Met Asp Pro Asn Gly Leu Ser
            180                 185                 190

Asp Pro Tyr Val Lys Leu Lys Leu Ile Pro Asp Pro Lys Asn Glu Ser
        195                 200                 205

Lys Gln Lys Thr Lys Thr Ile Arg Ser Thr Leu Asn Pro Gln Trp Asn
    210                 215                 220

Glu Ser Phe Thr Phe Lys Leu Lys Pro Ser Asp Lys Asp Arg Arg Leu
225                 230                 235                 240

Ser Val Glu Ile Trp Asp Trp Asp Arg Thr Thr Arg Asn Asp Phe Met
                245                 250                 255

Gly Ser Leu Ser Phe Gly Val Ser Glu Leu Met Lys Met Pro Ala Ser
            260                 265                 270

Gly Trp Tyr Lys Leu Leu Asn Gln Glu Glu Gly Glu Tyr Tyr Asn Val
        275                 280                 285

Pro Ile Pro Glu Gly Asp Glu Gly Asn Met Glu Leu Arg Gln Lys
    290                 295                 300

Phe Glu Lys Ala Lys Leu Gly Pro Ala Gly Asn Lys Val Ile Ser Pro
305                 310                 315                 320

Ser Glu Asp Arg Lys Gln Pro Ser Asn Asn Leu Asp Arg Val Lys Leu
                325                 330                 335

Thr Asp Phe Asn Phe Leu Met Val Leu Gly Lys Gly Ser Phe Gly Lys
            340                 345                 350

Val Met Leu Ala Asp Arg Lys Gly Thr Glu Glu Leu Tyr Ala Ile Lys
        355                 360                 365
```

-continued

```
Ile Leu Lys Lys Asp Val Val Ile Gln Asp Asp Val Glu Cys Thr
    370                 375                 380
Met Val Glu Lys Arg Val Leu Ala Leu Leu Asp Lys Pro Pro Phe Leu
385                 390                 395                 400
Thr Gln Leu His Ser Cys Phe Gln Thr Val Asp Arg Leu Tyr Phe Val
                    405                 410                 415
Met Glu Tyr Val Asn Gly Gly Asp Leu Met Tyr His Ile Gln Gln Val
                420                 425                 430
Gly Lys Phe Lys Glu Pro Gln Ala Val Phe Tyr Ala Ala Glu Ile Ser
            435                 440                 445
Ile Gly Leu Phe Phe Leu His Lys Arg Gly Ile Ile Tyr Arg Asp Leu
450                 455                 460
Lys Leu Asp Asn Val Met Leu Asp Ser Glu Gly His Ile Lys Ile Ala
465                 470                 475                 480
Asp Phe Gly Met Cys Lys Glu His Met Met Asp Gly Val Thr Thr Arg
                485                 490                 495
Thr Phe Cys Gly Thr Pro Asp Tyr Ile Ala Pro Glu Ile Ile Ala Tyr
            500                 505                 510
Gln Pro Tyr Gly Lys Ser Val Asp Trp Trp Ala Tyr Gly Val Leu Leu
        515                 520                 525
Tyr Glu Met Leu Ala Gly Gln Pro Pro Phe Asp Gly Glu Asp Glu Asp
530                 535                 540
Glu Leu Phe Gln Ser Ile Met Glu His Asn Val Ser Tyr Pro Lys Ser
545                 550                 555                 560
Leu Ser Lys Glu Ala Val Ser Val Cys Lys Gly Leu Met Thr Lys His
                565                 570                 575
Pro Ala Lys Arg Leu Gly Cys Gly Pro Glu Gly Glu Arg Asp Val Arg
            580                 585                 590
Glu His Ala Phe Phe Arg Arg Ile Asp Trp Glu Lys Leu Glu Asn Arg
        595                 600                 605
Glu Ile Gln Pro Pro Phe Lys Pro Lys Val Cys Gly Lys Gly Ala Glu
610                 615                 620
Asn Phe Asp Lys Phe Phe Thr Arg Gly Gln Pro Val Leu Thr Pro Pro
625                 630                 635                 640
Asp Gln Leu Val Ile Ala Asn Ile Asp Gln Ser Asp Phe Glu Gly Phe
                645                 650                 655
Ser Tyr Val Asn Pro Gln Phe Val His Pro Ile Leu Gln Ser Ala Val
            660                 665                 670
```

<210> SEQ ID NO 2
<211> LENGTH: 257
<212> TYPE: PRT
<213> ORGANISM: Homo sapiens

<400> SEQUENCE: 2

```
Phe Asn Phe Leu Met Val Leu Gly Lys Gly Ser Phe Gly Lys Val Met
1               5                   10                  15
Leu Ala Asp Arg Lys Gly Thr Glu Glu Leu Tyr Ala Ile Lys Ile Leu
                20                  25                  30
Lys Lys Asp Val Val Ile Gln Asp Asp Val Glu Cys Thr Met Val
            35                  40                  45
Glu Lys Arg Val Leu Ala Leu Leu Asp Lys Pro Pro Phe Leu Thr Gln
        50                  55                  60
Leu His Ser Cys Phe Gln Thr Val Asp Arg Leu Tyr Phe Val Met Glu
65                  70                  75                  80
```

```
Tyr Val Asn Gly Gly Asp Leu Met Tyr His Ile Gln Gln Val Gly Lys
                85                  90                  95

Phe Lys Glu Pro Gln Ala Val Phe Tyr Ala Ala Glu Ile Ser Ile Gly
            100                 105                 110

Leu Phe Phe Leu His Lys Arg Gly Ile Ile Tyr Arg Asp Leu Lys Leu
        115                 120                 125

Asp Asn Val Met Leu Asp Ser Glu Gly His Ile Lys Ile Ala Asp Phe
    130                 135                 140

Gly Met Cys Lys Glu His Met Met Asp Gly Val Thr Thr Arg Thr Phe
145                 150                 155                 160

Cys Gly Thr Pro Asp Tyr Ile Ala Pro Glu Ile Ile Ala Tyr Gln Pro
                165                 170                 175

Tyr Gly Lys Ser Val Asp Trp Trp Ala Tyr Gly Val Leu Leu Tyr Glu
            180                 185                 190

Met Leu Ala Gly Gln Pro Pro Phe Asp Gly Glu Asp Glu Asp Glu Leu
        195                 200                 205

Phe Gln Ser Ile Met Glu His Asn Val Ser Tyr Pro Lys Ser Leu Ser
    210                 215                 220

Lys Glu Ala Val Ser Val Cys Lys Gly Leu Met Thr Lys His Pro Ala
225                 230                 235                 240

Lys Arg Leu Gly Cys Gly Pro Glu Gly Glu Arg Asp Val Arg Glu His
                245                 250                 255

Ala

<210> SEQ ID NO 3
<211> LENGTH: 12
<212> TYPE: PRT
<213> ORGANISM: artificial sequence
<220> FEATURE:
<223> OTHER INFORMATION: segment of kinase domain of alphaPKC

<400> SEQUENCE: 3

Val Glu Cys Thr Met Val Glu Lys Arg Val Leu Ala
1               5                   10

<210> SEQ ID NO 4
<211> LENGTH: 8
<212> TYPE: PRT
<213> ORGANISM: artificial sequence
<220> FEATURE:
<223> OTHER INFORMATION: segment of kinase domain of alphaPKC

<400> SEQUENCE: 4

Leu Met Tyr His Ile Gln Gln Val
1               5

<210> SEQ ID NO 5
<211> LENGTH: 4
<212> TYPE: PRT
<213> ORGANISM: artificial sequence
<220> FEATURE:
<223> OTHER INFORMATION: segment of kinase domain of alphaPKC

<400> SEQUENCE: 5

Pro Glu Ile Ile
1

<210> SEQ ID NO 6
<211> LENGTH: 16
<212> TYPE: PRT
```

```
<213> ORGANISM: artificial sequence
<220> FEATURE:
<223> OTHER INFORMATION: segment of kinase domain of alphaPKC

<400> SEQUENCE: 6

Ser Val Asp Trp Trp Ala Tyr Gly Val Leu Leu Tyr Glu Met Leu Ala
1               5                   10                  15

<210> SEQ ID NO 7
<211> LENGTH: 12
<212> TYPE: PRT
<213> ORGANISM: artificial sequence
<220> FEATURE:
<223> OTHER INFORMATION: segment of kinase domain of alphaPKC

<400> SEQUENCE: 7

Glu Asp Glu Asp Glu Leu Phe Gln Ser Ile Met Glu
1               5                   10

<210> SEQ ID NO 8
<211> LENGTH: 7
<212> TYPE: PRT
<213> ORGANISM: artificial sequence
<220> FEATURE:
<223> OTHER INFORMATION: segment of kinase domain of alphaPKC

<400> SEQUENCE: 8

Gly Glu Arg Asp Val Arg Glu
1               5

<210> SEQ ID NO 9
<211> LENGTH: 12
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (5)..(5)
<223> OTHER INFORMATION: Xaa is any amino acid except R, M and P

<400> SEQUENCE: 9

Val Glu Cys Thr Xaa Val Glu Lys Arg Val Leu Ala
1               5                   10

<210> SEQ ID NO 10
<211> LENGTH: 12
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (9)..(9)
<223> OTHER INFORMATION: Xaa is any amino acid except M, P and R

<400> SEQUENCE: 10

Val Glu Cys Thr Met Val Glu Lys Xaa Val Leu Ala
1               5                   10

<210> SEQ ID NO 11
<211> LENGTH: 12
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (5)..(5)
```

<223> OTHER INFORMATION: Xaa is any amino acid except M, P and R
<220> FEATURE:
<221> NAME/KEY: MISC_FEATURE
<222> LOCATION: (9)..(9)
<223> OTHER INFORMATION: Xaa is any amino acid except M, P and R

<400> SEQUENCE: 11

Val Glu Cys Thr Xaa Val Glu Lys Xaa Val Leu Ala
1               5                   10

<210> SEQ ID NO 12
<211> LENGTH: 8
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (2)..(2)
<223> OTHER INFORMATION: Xaa is any amino acid except M, P and R

<400> SEQUENCE: 12

Leu Xaa Tyr His Ile Gln Gln Val
1               5

<210> SEQ ID NO 13
<211> LENGTH: 16
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (14)..(14)
<223> OTHER INFORMATION: Xaa is any amino acid except M, P and R

<400> SEQUENCE: 13

Ser Val Asp Trp Trp Ala Tyr Gly Val Leu Leu Tyr Glu Xaa Leu Ala
1               5                   10                  15

<210> SEQ ID NO 14
<211> LENGTH: 12
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (11)..(11)
<223> OTHER INFORMATION: Xaa is any amino acid except M, P and R

<400> SEQUENCE: 14

Glu Asp Glu Asp Glu Leu Phe Gln Ser Ile Xaa Glu
1               5                   10

<210> SEQ ID NO 15
<211> LENGTH: 7
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (3)..(3)
<223> OTHER INFORMATION: Xaa is any amino acid except M, P and R

<400> SEQUENCE: 15

Gly Glu Xaa Asp Val Arg Glu
1               5

```
<210> SEQ ID NO 16
<211> LENGTH: 7
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (6)..(6)
<223> OTHER INFORMATION: Xaa is any amino acid except M, P and R

<400> SEQUENCE: 16

Gly Glu Arg Asp Val Xaa Glu
1               5

<210> SEQ ID NO 17
<211> LENGTH: 7
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (3)..(3)
<223> OTHER INFORMATION: Xaa is any amino acid except M, P and R
<220> FEATURE:
<221> NAME/KEY: MISC_FEATURE
<222> LOCATION: (6)..(6)
<223> OTHER INFORMATION: Xaa is any amino acid except M, P and R

<400> SEQUENCE: 17

Gly Glu Xaa Asp Val Xaa Glu
1               5

<210> SEQ ID NO 18
<211> LENGTH: 4
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (1)..(1)
<223> OTHER INFORMATION: Xaa is any amino acid except M, P and R

<400> SEQUENCE: 18

Xaa Glu Ile Ile
1

<210> SEQ ID NO 19
<211> LENGTH: 12
<212> TYPE: PRT
<213> ORGANISM: artificial sequence
<220> FEATURE:
<223> OTHER INFORMATION: mutated segment of kinase domain of alphaPKC

<400> SEQUENCE: 19

Val Glu Cys Thr Thr Val Glu Lys Glu Val Leu Ala
1               5                   10

<210> SEQ ID NO 20
<211> LENGTH: 25
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (5)..(5)
<223> OTHER INFORMATION: Xaa is any amino acid except M, P and R
```

-continued

```
<220> FEATURE:
<221> NAME/KEY: MISC_FEATURE
<222> LOCATION: (9)..(9)
<223> OTHER INFORMATION: Xaa is any amino acid except M, P and R
<220> FEATURE:
<221> NAME/KEY: MISC_FEATURE
<222> LOCATION: (17)..(18)
<223> OTHER INFORMATION: Xaa is any amino acid except M, P and R

<400> SEQUENCE: 20

Val Glu Cys Thr Xaa Val Glu Lys Xaa Val Leu Ala Leu Leu Asp Lys
1               5                   10                  15

Xaa Xaa Phe Leu Thr Gln Leu His Ser
            20                  25

<210> SEQ ID NO 21
<211> LENGTH: 25
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (17)..(18)
<223> OTHER INFORMATION: Xaa is any amino acid except M, P and R

<400> SEQUENCE: 21

Val Glu Cys Thr Met Val Glu Lys Arg Val Leu Ala Leu Leu Asp Lys
1               5                   10                  15

Xaa Xaa Phe Leu Thr Gln Leu His Ser
            20                  25

<210> SEQ ID NO 22
<211> LENGTH: 25
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (5)..(5)
<223> OTHER INFORMATION: Xaa is any amino acid except M, P and R

<400> SEQUENCE: 22

Val Glu Cys Thr Xaa Val Glu Lys Arg Val Leu Ala Leu Leu Asp Lys
1               5                   10                  15

Pro Pro Phe Leu Thr Gln Leu His Ser
            20                  25

<210> SEQ ID NO 23
<211> LENGTH: 25
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (9)..(9)
<223> OTHER INFORMATION: Xaa is any amino acid except M, P and R

<400> SEQUENCE: 23

Val Glu Cys Thr Met Val Glu Lys Xaa Val Leu Ala Leu Leu Asp Lys
1               5                   10                  15

Pro Pro Phe Leu Thr Gln Leu His Ser
            20                  25

<210> SEQ ID NO 24
```

```
<211> LENGTH: 13
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (6)..(6)
<223> OTHER INFORMATION: Xaa is any amino acid derivative suitable for
      stapling
<220> FEATURE:
<221> NAME/KEY: MISC_FEATURE
<222> LOCATION: (13)..(13)
<223> OTHER INFORMATION: Xaa is any amino acid derivative suitable for
      stapling

<400> SEQUENCE: 24

Val Glu Cys Thr Met Xaa Glu Lys Arg Val Leu Ala Xaa
1               5                   10

<210> SEQ ID NO 25
<211> LENGTH: 13
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (5)..(5)
<223> OTHER INFORMATION: Xaa is any amino acid except M, P and R
<220> FEATURE:
<221> NAME/KEY: MISC_FEATURE
<222> LOCATION: (6)..(6)
<223> OTHER INFORMATION: Xaa is any amino acid derivative suitable for
      stapling
<220> FEATURE:
<221> NAME/KEY: MISC_FEATURE
<222> LOCATION: (13)..(13)
<223> OTHER INFORMATION: Xaa is any amino acid derivative suitable for
      stapling

<400> SEQUENCE: 25

Val Glu Cys Thr Xaa Xaa Glu Lys Arg Val Leu Ala Xaa
1               5                   10

<210> SEQ ID NO 26
<211> LENGTH: 13
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (6)..(6)
<223> OTHER INFORMATION: Xaa is any amino acid derivative suitable for
      stapling
<220> FEATURE:
<221> NAME/KEY: MISC_FEATURE
<222> LOCATION: (9)..(9)
<223> OTHER INFORMATION: Xaa is any amino acid except M, P and R
<220> FEATURE:
<221> NAME/KEY: MISC_FEATURE
<222> LOCATION: (13)..(13)
<223> OTHER INFORMATION: Xaa is any amino acid derivative suitable for
      stapling

<400> SEQUENCE: 26

Val Glu Cys Thr Met Xaa Glu Lys Xaa Val Leu Ala Xaa
1               5                   10

<210> SEQ ID NO 27
<211> LENGTH: 13
<212> TYPE: PRT
```

```
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (5)..(5)
<223> OTHER INFORMATION: Xaa is any amino acid except M, P and R
<220> FEATURE:
<221> NAME/KEY: MISC_FEATURE
<222> LOCATION: (6)..(6)
<223> OTHER INFORMATION: Xaa is any amino acid derivative suitable for
      stapling
<220> FEATURE:
<221> NAME/KEY: MISC_FEATURE
<222> LOCATION: (9)..(9)
<223> OTHER INFORMATION: Xaa is any amino acid except M, P and R
<220> FEATURE:
<221> NAME/KEY: MISC_FEATURE
<222> LOCATION: (13)..(13)
<223> OTHER INFORMATION: Xaa is any amino acid derivative suitable for
      stapling

<400> SEQUENCE: 27

Val Glu Cys Thr Xaa Xaa Glu Lys Xaa Val Leu Ala Xaa
1               5                   10

<210> SEQ ID NO 28
<211> LENGTH: 25
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (5)..(5)
<223> OTHER INFORMATION: Xaa is any amino acid except M, P and R
<220> FEATURE:
<221> NAME/KEY: MISC_FEATURE
<222> LOCATION: (6)..(6)
<223> OTHER INFORMATION: Xaa is any amino acid derivative suitable for
      stapling
<220> FEATURE:
<221> NAME/KEY: MISC_FEATURE
<222> LOCATION: (9)..(9)
<223> OTHER INFORMATION: Xaa is any amino acid except M, P and R
<220> FEATURE:
<221> NAME/KEY: MISC_FEATURE
<222> LOCATION: (13)..(13)
<223> OTHER INFORMATION: Xaa is any amino acid derivative suitable for
      stapling
<220> FEATURE:
<221> NAME/KEY: MISC_FEATURE
<222> LOCATION: (17)..(18)
<223> OTHER INFORMATION: Xaa is any amino acid except M, P and R

<400> SEQUENCE: 28

Val Glu Cys Thr Xaa Xaa Glu Lys Xaa Val Leu Ala Xaa Leu Asp Lys
1               5                   10                  15

Xaa Xaa Phe Leu Thr Gln Leu His Ser
            20                  25

<210> SEQ ID NO 29
<211> LENGTH: 25
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (6)..(6)
<223> OTHER INFORMATION: Xaa is any amino acid derivative suitable for
      stapling
<220> FEATURE:
<221> NAME/KEY: MISC_FEATURE
```

-continued

```
<222> LOCATION: (13)..(13)
<223> OTHER INFORMATION: Xaa is any amino acid derivative suitable for
      stapling
<220> FEATURE:
<221> NAME/KEY: MISC_FEATURE
<222> LOCATION: (17)..(18)
<223> OTHER INFORMATION: Xaa is any amino acid except M, P and R

<400> SEQUENCE: 29

Val Glu Cys Thr Met Xaa Glu Lys Arg Val Leu Ala Xaa Leu Asp Lys
1               5                  10                  15

Xaa Xaa Phe Leu Thr Gln Leu His Ser
            20                  25

<210> SEQ ID NO 30
<211> LENGTH: 25
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (5)..(5)
<223> OTHER INFORMATION: Xaa is any amino acid except M, P and R
<220> FEATURE:
<221> NAME/KEY: MISC_FEATURE
<222> LOCATION: (6)..(6)
<223> OTHER INFORMATION: Xaa is any amino acid derivative suitable for
      stapling
<220> FEATURE:
<221> NAME/KEY: MISC_FEATURE
<222> LOCATION: (13)..(13)
<223> OTHER INFORMATION: Xaa is any amino acid derivative suitable for
      stapling

<400> SEQUENCE: 30

Val Glu Cys Thr Xaa Xaa Glu Lys Arg Val Leu Ala Xaa Leu Asp Lys
1               5                  10                  15

Pro Pro Phe Leu Thr Gln Leu His Ser
            20                  25

<210> SEQ ID NO 31
<211> LENGTH: 25
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (6)..(6)
<223> OTHER INFORMATION: Xaa is any amino acid derivative suitable for
      stapling
<220> FEATURE:
<221> NAME/KEY: MISC_FEATURE
<222> LOCATION: (9)..(9)
<223> OTHER INFORMATION: Xaa is any amino acid except M, P and R
<220> FEATURE:
<221> NAME/KEY: MISC_FEATURE
<222> LOCATION: (13)..(13)
<223> OTHER INFORMATION: Xaa is any amino acid derivative suitable for
      stapling

<400> SEQUENCE: 31

Val Glu Cys Thr Met Xaa Glu Lys Xaa Val Leu Ala Xaa Leu Asp Lys
1               5                  10                  15

Pro Pro Phe Leu Thr Gln Leu His Ser
            20                  25

<210> SEQ ID NO 32
<211> LENGTH: 25
```

```
<212> TYPE: PRT
<213> ORGANISM: artificial sequence
<220> FEATURE:
<223> OTHER INFORMATION: mutated segment of kinase domain of alphaPKC

<400> SEQUENCE: 32

Val Glu Cys Thr Thr Arg Glu Lys Glu Val Leu Ala Ser Leu Asp Lys
1               5                   10                  15

Ala Ala Phe Leu Thr Gln Leu His Ser
            20                  25

<210> SEQ ID NO 33
<211> LENGTH: 8
<212> TYPE: PRT
<213> ORGANISM: artificial sequence
<220> FEATURE:
<223> OTHER INFORMATION: protein transduction domain

<400> SEQUENCE: 33

Arg Arg Arg Arg Arg Arg Arg Arg
1               5

<210> SEQ ID NO 34
<211> LENGTH: 15
<212> TYPE: PRT
<213> ORGANISM: artificial sequence
<220> FEATURE:
<223> OTHER INFORMATION: protein transduction domain

<400> SEQUENCE: 34

Arg Arg Pro Arg Arg Pro Arg Arg Pro Arg Arg Pro Arg Arg Pro
1               5                   10                  15

<210> SEQ ID NO 35
<211> LENGTH: 16
<212> TYPE: PRT
<213> ORGANISM: artificial sequence
<220> FEATURE:
<223> OTHER INFORMATION: penetratin peptide

<400> SEQUENCE: 35

Arg Gln Ile Lys Ile Trp Phe Gln Asn Arg Arg Met Lys Trp Lys Lys
1               5                   10                  15

<210> SEQ ID NO 36
<211> LENGTH: 11
<212> TYPE: PRT
<213> ORGANISM: artificial sequence
<220> FEATURE:
<223> OTHER INFORMATION: HIV-tat

<400> SEQUENCE: 36

Tyr Gly Arg Lys Lys Arg Arg Gln Arg Arg Arg
1               5                   10

<210> SEQ ID NO 37
<211> LENGTH: 20
<212> TYPE: DNA
<213> ORGANISM: artificial sequence
<220> FEATURE:
<223> OTHER INFORMATION: primer

<400> SEQUENCE: 37
tgctttggtt tctgggactt                                           20

<210> SEQ ID NO 38
```

-continued

```
<211> LENGTH: 20
<212> TYPE: DNA
<213> ORGANISM: artificial sequence
<220> FEATURE:
<223> OTHER INFORMATION: primer

<400> SEQUENCE: 38
gctctagccg aacacgaatc                                              20

<210> SEQ ID NO 39
<211> LENGTH: 22
<212> TYPE: DNA
<213> ORGANISM: artificial sequence
<220> FEATURE:
<223> OTHER INFORMATION: primer

<400> SEQUENCE: 39
tggacaaagt agacggagtg tc                                           22

<210> SEQ ID NO 40
<211> LENGTH: 20
<212> TYPE: DNA
<213> ORGANISM: artificial sequence
<220> FEATURE:
<223> OTHER INFORMATION: primer

<400> SEQUENCE: 40
tagcaaggcc tgtcccatac                                              20

<210> SEQ ID NO 41
<211> LENGTH: 20
<212> TYPE: DNA
<213> ORGANISM: artificial sequence
<220> FEATURE:
<223> OTHER INFORMATION: primer

<400> SEQUENCE: 41
tgagaacttg ccaccgtatg                                              20

<210> SEQ ID NO 42
<211> LENGTH: 20
<212> TYPE: DNA
<213> ORGANISM: artificial sequence
<220> FEATURE:
<223> OTHER INFORMATION: primer

<400> SEQUENCE: 42
ggcaggtagg cccctatatc                                              20

<210> SEQ ID NO 43
<211> LENGTH: 20
<212> TYPE: DNA
<213> ORGANISM: artificial sequence
<220> FEATURE:
<223> OTHER INFORMATION: primer

<400> SEQUENCE: 43
gtttcatccg ggtcttcatc                                              20

<210> SEQ ID NO 44
<211> LENGTH: 20
<212> TYPE: DNA
<213> ORGANISM: artificial sequence
<220> FEATURE:
<223> OTHER INFORMATION: primer

<400> SEQUENCE: 44
```

```
gtgtctgtgc cctcgaaaat                                               20

<210> SEQ ID NO 45
<211> LENGTH: 20
<212> TYPE: DNA
<213> ORGANISM: artificial sequence
<220> FEATURE:
<223> OTHER INFORMATION: primer

<400> SEQUENCE: 45
aagttctctg cctcccgatt                                               20

<210> SEQ ID NO 46
<211> LENGTH: 20
<212> TYPE: DNA
<213> ORGANISM: artificial sequence
<220> FEATURE:
<223> OTHER INFORMATION: primer

<400> SEQUENCE: 46
caaagcgttg ctggaagttt                                               20

<210> SEQ ID NO 47
<211> LENGTH: 20
<212> TYPE: DNA
<213> ORGANISM: artificial sequence
<220> FEATURE:
<223> OTHER INFORMATION: primer

<400> SEQUENCE: 47
tcgattccct cctacactgc                                               20

<210> SEQ ID NO 48
<211> LENGTH: 20
<212> TYPE: DNA
<213> ORGANISM: artificial sequence
<220> FEATURE:
<223> OTHER INFORMATION: primer

<400> SEQUENCE: 48
ttggtggtac tggctcatca                                               20

<210> SEQ ID NO 49
<211> LENGTH: 25
<212> TYPE: PRT
<213> ORGANISM: artificial sequence
<220> FEATURE:
<223> OTHER INFORMATION: PATAD

<400> SEQUENCE: 49

Val Glu Cys Thr Met Ala Glu Lys Arg Val Leu Ala Ala Leu Asp Lys
1               5                   10                  15

Pro Pro Phe Leu Thr Gln Leu His Ser
            20                  25

<210> SEQ ID NO 50
<211> LENGTH: 13
<212> TYPE: PRT
<213> ORGANISM: artificial
<220> FEATURE:
<223> OTHER INFORMATION: segment of kinase domain of alphaPKC

<400> SEQUENCE: 50

Glu Cys Thr Met Val Glu Lys Lys Val Leu Ala Leu Leu
1               5                   10
```

```
<210> SEQ ID NO 51
<211> LENGTH: 15
<212> TYPE: PRT
<213> ORGANISM: artificial
<220> FEATURE:
<223> OTHER INFORMATION: mutated segment of kinase domain of alphaPKC

<400> SEQUENCE: 51

Ser Val Glu Trp Trp Ala Tyr Gly Leu Leu Tyr Glu Met Leu Ala
1               5                   10                  15

<210> SEQ ID NO 52
<211> LENGTH: 15
<212> TYPE: PRT
<213> ORGANISM: artificial
<220> FEATURE:
<223> OTHER INFORMATION: mutated segment of kinase domain of alphaPKC
<220> FEATURE:
<221> NAME/KEY: MISC_FEATURE
<222> LOCATION: (3)..(3)
<223> OTHER INFORMATION: Xaa is any amino acid except M, P and R

<400> SEQUENCE: 52

Ser Val Xaa Trp Trp Ala Tyr Gly Leu Leu Tyr Glu Met Leu Ala
1               5                   10                  15

<210> SEQ ID NO 53
<211> LENGTH: 24
<212> TYPE: PRT
<213> ORGANISM: artificial
<220> FEATURE:
<223> OTHER INFORMATION: mutated segment of kinase domain of alphaPKC
<220> FEATURE:
<221> NAME/KEY: MISC_FEATURE
<222> LOCATION: (6)..(6)
<223> OTHER INFORMATION: Xaa is any amino acid derivative suitable for
      stapling
<220> FEATURE:
<221> NAME/KEY: MISC_FEATURE
<222> LOCATION: (13)..(13)
<223> OTHER INFORMATION: Xaa is any amino acid derivative suitable for
      stapling

<400> SEQUENCE: 53

Val Glu Cys Thr Thr Xaa Glu Lys Glu Val Leu Ala Xaa Leu Asp Lys
1               5                   10                  15

Ala Ala Phe Leu Thr Gln His Ser
            20

<210> SEQ ID NO 54
<211> LENGTH: 19
<212> TYPE: PRT
<213> ORGANISM: artificial
<220> FEATURE:
<223> OTHER INFORMATION: mutated segment of kinase domain of alphaPKC
<220> FEATURE:
<221> NAME/KEY: MISC_FEATURE
<222> LOCATION: (6)..(6)
<223> OTHER INFORMATION: Xaa is any amino acid derivative suitable for
      stapling
<220> FEATURE:
<221> NAME/KEY: MISC_FEATURE
<222> LOCATION: (13)..(13)
<223> OTHER INFORMATION: Xaa is any amino acid derivative suitable for
      stapling

<400> SEQUENCE: 54

Val Glu Cys Thr Thr Xaa Glu Lys Glu Val Leu Ala Xaa Leu Asp Lys
1               5                   10                  15
```

Ala Ala Phe

<210> SEQ ID NO 55
<211> LENGTH: 19
<212> TYPE: PRT
<213> ORGANISM: artificial
<220> FEATURE:
<223> OTHER INFORMATION: mutated segment of kinase domain of alphaPKC
<220> FEATURE:
<221> NAME/KEY: MISC_FEATURE
<222> LOCATION: (6)..(6)
<223> OTHER INFORMATION: Xaa is any amino acid derivative suitable for
      stapling
<220> FEATURE:
<221> NAME/KEY: MISC_FEATURE
<222> LOCATION: (13)..(13)
<223> OTHER INFORMATION: Xaa is any amino acid derivative suitable for
      stapling

<400> SEQUENCE: 55

Val Glu Gly Thr Thr Xaa Glu Lys Glu Val Leu Ala Xaa Leu Asp Lys
1               5                   10                  15

Ala Ala Phe

<210> SEQ ID NO 56
<211> LENGTH: 13
<212> TYPE: PRT
<213> ORGANISM: artificial
<220> FEATURE:
<223> OTHER INFORMATION: mutated segment of kinase domain of alphaPKC
<220> FEATURE:
<221> NAME/KEY: MISC_FEATURE
<222> LOCATION: (4)..(4)
<223> OTHER INFORMATION: Xaa is any amino acid derivative suitable for
      stapling
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: Xaa is any amino acid derivative suitable for
      stapling

<400> SEQUENCE: 56

Glu Cys Thr Thr Xaa Glu Lys Glu Val Leu Ala Xaa Leu
1               5                   10

<210> SEQ ID NO 57
<211> LENGTH: 13
<212> TYPE: PRT
<213> ORGANISM: artificial
<220> FEATURE:
<223> OTHER INFORMATION: mutated segment of kinase domain of alphaPKC
<220> FEATURE:
<221> NAME/KEY: MISC_FEATURE
<222> LOCATION: (4)..(4)
<223> OTHER INFORMATION: Xaa is any amino acid derivative suitable for
      stapling
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: Xaa is any amino acid derivative suitable for
      stapling

<400> SEQUENCE: 57

Glu Cys Thr Met Xaa Glu Lys Lys Val Leu Ala Xaa Leu
1               5                   10

PEPTIDES FOR TREATMENT AND PREVENTION OF DIABETES AND ASSOCIATED DISORDERS

CROSS-REFERENCE TO RELATED APPLICATION

This application is the U.S. national stage application of International Patent Application No. PCT/EP2019/086573, filed Dec. 20, 2019.

The Sequence Listing for this application is labeled "Seq-List.txt" which was created on Jun. 14, 2021 and is 28 KB. The entire content of the sequence listing is incorporated herein by reference in its entirety.

FIELD OF THE INVENTION

The present invention relates to the field of the medicine. More particularly, it relates to treatment of diabetes and the associated disorders.

BACKGROUND OF THE INVENTION

Diabetes mellitus or diabetes is a group of metabolic diseases in which a person has high blood sugar, either because the pancreas does not produce enough insulin, or because cells do not respond to the insulin that is produced.

There are three main types of diabetes:
Type 1 results from the body's failure to produce insulin, and currently requires the person to inject insulin or wear an insulin pump.
Type 2 results from insulin resistance, a condition in which cells fail to use insulin properly.
The third one is called gestational diabetes and occurs with pregnant women.

Rates of type 2 diabetes have increased markedly since 1960 in parallel with obesity: As of 2010 there are approximately 285 million people with the disease compared to around 30 million in 1985. Long-term complications from high blood sugar can include heart diseases, strokes, diabetic retinopathy, chronic renal failure which may require dialysis and poor circulation in the limbs leading to amputations. Nonketotic hyperosmolar coma may occur.

It has been reported that hyperglycemia participates in the onset and progressive impairment of diabetes mellitus, i.e., glucose toxicity theory. Namely, chronic hyperglycemia leads to decrease insulin secretion and further to decrease insulin sensitivity, and as a result, the blood glucose concentration is increased so that diabetes mellitus is self-exacerbated. Therefore, by treating hyperglycemia, the aforementioned self-exacerbating cycle is interrupted so that the prophylaxis or treatment of diabetes mellitus is made possible.

Unfortunately, existing treatments do not succeed in restoring normoglycaemia in the long term, since beta-cell function declines over time. Moreover, there is presently no single drug able to reverse all aspects of the disease.

The progressive nature of type 2 diabetes means that many patients will eventually require a combination of oral hypoglycaemic medication, possibly together with insulin and/or exenatide injections. Anti-diabetic agents have been developed in order to counteract the main mechanisms involved in type 2 diabetes: insulin resistance (biguanides and thiazolidinediones) and insulin secretion (sulfonylureas, glinides, dipeptidylpeptidase-4 inhibitors, glucagon-like peptide 1 receptor agonists), agents that delay absorption of glucose by gastrointestinal tract or promote weight loss and newer agents that promote renal glucose excretion. However, most of these medications have been shown to have deleterious side effects such as weight gain, peripheral edema or congestive heart failure and there is a major problem with a loss of effectiveness of these agents with long-term use. Thus, despite the increasing number of therapeutic options for glycaemic control, there is a need for alternative and improved medications for the treatment of diabetes and related conditions.

SUMMARY OF THE INVENTION

Surprisingly, the inventors provide peptides from the kinase domain of the PKCα and derivatives thereof which specifically improves glucose tolerance in diet induced obese mice. The peptides are capable of decreasing the expression of Solute Carrier Family 27 Member 2 (SLC27A2) commonly known as FATP2 (Fatty acid transport protein 2) in adipose tissue. The peptides are capable of decreasing glycated albumin in plasma of an animal model, the glycated albumin being a well-known biomarker of diabetes.

Accordingly, the present invention relates to a peptide for use for treating diabetes and associated disorders, wherein
the peptide is capable of decreasing specifically the FATP2 expression in adipose tissue, in particular in a mammal, especially human adipose tissue;
the peptide does not simultaneously comprise one methionine, one proline and one arginine;
the peptide adopts a secondary structure which is a helix, preferably an alpha helix; and
the peptide comprises, consists essentially in or consists in a sequence from a segment of at least 5, 6, 7, 8, 9, 10, 11, 12, 13, 14, 15, 16, 17, 18, 19, 20, 21, 22, 23 or 25 consecutive residues of the kinase domain of α PKC (Protein Kinase C) or a segment from 5 to 40 consecutive residues of the kinase domain of α PKC (Protein Kinase C);
the peptide has a length from 5 to 80 amino acids or from 5 to 60 amino acids or from 5 to 40 amino acids, and
the peptide sequence may comprise 1, 2, 3, 4, or 5 modification(s) of an amino acid selected from substitution(s), deletion(s), addition(s), and a mixture thereof within said sequence of a segment of the kinase domain of the PKC.

Preferably, the peptide is modified by a chemical cross-linking process such as stapling.

Preferably, the peptide has a length of at least 5 amino acids and less than 40 amino acids, preferably a length of at least 5 amino acids and less than 30 amino acids, more preferably of at least 5 amino acids and less than 25 amino acids.

Preferably, the peptide is capable of decreasing or preventing the interaction between ALMS1 and αPKC.

Optionally, the peptide sequence comprises, consists essentially in or consists in at least one of the following sequences: VECTMVEKRVLA (SEQ ID NO: 3) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; VECTXVEKRVLA (SEQ ID NO: 9) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; VECTMVEKXVLA (SEQ ID NO: 10) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; VECTXVEKXVLA (SEQ ID NO: 11) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; LMYHIQQV (SEQ ID NO: 4) with optionally 1, 2, or 3 modification(s) of an amino acid selected from substitution(s) deletion(s), addition(s), and a mixture thereof; LXYHIQQV (SEQ ID NO: 12) with optionally 1, 2, or 3 modification(s) of an amino acid selected from substitution(s) deletion(s), addition(s), and a mixture thereof; LDN; SVDWWAYGVLLYEMLA (SEQ ID NO: 6) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; SVDWWAYGVLLYEXLA (SEQ ID NO: 13) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; SVXWWAYGLLYEMLA (SEQ ID NO: 52) optionally comprising from 1 to 5 modification(s) of an amino acid selected from substitution(s), deletion(s), addition(s), and a mixture thereof; EDEDELFQSIME (SEQ ID NO: 7) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; EDEDELFQSIXE (SEQ ID NO: 14) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; GERDVRE (SEQ ID NO: 8) with optionally 1, 2, or 3 modification(s) of an amino acid selected from substitution(s) deletion(s), addition(s), and a mixture thereof; GEXDVRE (SEQ ID NO: 15) with optionally 1, 2, or 3 modification(s) of an amino acid selected from substitution(s) deletion(s), addition(s), and a mixture thereof; GERDVXE (SEQ ID NO: 16) with optionally 1, 2, or 3 modification(s) of an amino acid selected from substitution(s) deletion(s), addition(s), and a mixture thereof; GEXDVXE (SEQ ID NO: 17) with optionally 1, 2, or 3 modification(s) of an amino acid selected from substitution(s) deletion(s), addition(s), and a mixture thereof; LDN; AFF; PDY; XDY; PEII (SEQ ID NO: 5); XEII (SEQ ID NO: 18); PAK; XAK; wherein X is any amino acid except M, P and R.

Optionally, the peptide sequence comprises, consists essentially in or consists in at least one of the following sequences: VECTMVEKRVLA (SEQ ID NO: 3) with optionally 1, 2, or 3 modification(s) of an amino acid selected from substitution(s) deletion(s), addition(s), and a mixture thereof; VECTXVEKRVLA (SEQ ID NO: 9) with optionally 1, 2, or 3 modification(s) of an amino acid selected from substitution(s) deletion(s), addition(s), and a mixture thereof; VECTMVEKXVLA (SEQ ID NO: 10) with optionally 1, 2, or 3 modification(s) of an amino acid selected from substitution(s) deletion(s), addition(s), and a mixture thereof; VECTXVEKXVLA (SEQ ID NO: 11) with optionally 1, 2, or 3 modification(s) of an amino acid selected from substitution(s) deletion(s), addition(s), and a mixture thereof; LMYHIQQV (SEQ ID NO: 4) with optionally 1, 2, or 3 modification(s) of an amino acid selected from substitution(s) deletion(s), addition(s), and a mixture thereof; LXYHIQQV (SEQ ID NO: 12) with optionally 1, 2, or 3 modification(s) of an amino acid selected from substitution(s) deletion(s), addition(s), and a mixture thereof; SVDWWAYGVLLYEMLA (SEQ ID NO: 6) with optionally 1, 2, or 3 modification(s) of an amino acid selected from substitution(s) deletion(s), addition(s), and a mixture thereof; SVDWWAYGVLLYEXLA (SEQ ID NO: 13) with optionally 1, 2, or 3 modification(s) of an amino acid selected from substitution(s) deletion(s), addition(s), and a mixture thereof; EDEDELFQSIME (SEQ ID NO: 7) with optionally 1, 2, or 3 modification(s) of an amino acid selected from substitution(s) deletion(s), addition(s), and a mixture thereof; EDEDELFQSIXE (SEQ ID NO: 14) with optionally 1, 2, or 3 modification(s) of an amino acid selected from substitution(s) deletion(s), addition(s), and a mixture thereof; GERDVRE (SEQ ID NO: 8) with optionally 1, 2, or 3 modification(s) of an amino acid selected from substitution(s) deletion(s), addition(s), and a mixture thereof; GEXDVRE (SEQ ID NO: 15) with optionally 1, 2, or 3 modification(s) of an amino acid selected from substitution(s) deletion(s), addition(s), and a mixture thereof; GERDVXE (SEQ ID NO: 16) with optionally 1, 2, or 3 modification(s) of an amino acid selected from substitution(s) deletion(s), addition(s), and a mixture thereof; GEXDVXE (SEQ ID NO: 17) with optionally 1, 2, or 3 modification(s) of an amino acid selected from substitution(s) deletion(s), addition(s), and a mixture thereof; wherein X is any amino acid except M, P and R.

Optionally, the peptide sequence comprises, consists essentially in or consists in at least one of the following sequences:

a) VECTXVEKXVLALLDKXXFLTQLHS (SEQ ID NO: 20) wherein X is any amino acid except M, P and R, preferably, an amino acid favorable to an α-helix secondary structure, more preferably selected from the group consisting of A, D, N, C, G, Q, E, H, L, K, F, S, W and Y, still more preferably A, D, N, G, Q, E, H, L, K, F, S, W and Y, with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof;

b) VECTMVEKRVLALLDKXXFLTQLHS (SEQ ID NO: 21) wherein X is any amino acid except M, P and R, preferably, an amino acid favorable to an α-helix secondary structure, more preferably selected from the group consisting of A, D, N, C, G, Q, E, H, L, K, F, S, W and Y, still more preferably A, D, N, G, Q, E, H, L, K, F, S, W and Y, with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof;

c) VECTXVEKRVLALLDKPPFLTQLHS (SEQ ID NO: 22) wherein X is any amino acid except M, P and R, preferably, an amino acid favorable to an α-helix secondary structure, more preferably selected from the group consisting of A, D, N, C, G, Q, E, H, L, K, F, S, W and Y, still more preferably A, D, N, G, Q, E, H, L, K, F, S, W and Y, with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof;

d) VECTMVEKXVLALLDKPPFLTQLHS (SEQ ID NO: 23) wherein X is any amino acid except M, P and R, preferably, an amino acid favorable to an α-helix secondary structure, more preferably selected from the group consisting of A, D, N, C, G, Q, E, H, L, K, F, S, W and Y, still more preferably A, D, N, G, Q, E, H, L, K, F, S, W and Y, with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof;

and the sequence of any segment of at least 5, 6, 7, 8, 9, 10, 11, 12, 13, 14, 15, 16, 17, 18, 19, 20, 21, 22, 23 or 25 consecutive residues of any sequence a) to d).

Optionally, the peptide sequence comprises, consists essentially in or consists in at least one of the following sequences:

VECTMXEKRVLAX (SEQ ID NO: 24)

VECTXXEKRVLAX (SEQ ID NO: 25)

VECTMXEKXVLAX (SEQ ID NO: 26)

VECTXXEKXVLAX (SEQ ID NO: 27)

VECTXXEKXVLAXLDKXXFLTQLHS (SEQ ID NO: 28)

VECTMXEKRVLAXLDKXXFLTQLHS (SEQ ID NO: 29)

VECTXXEKRVLAXLDKPPFLTQLHS (SEQ ID NO: 30)

VECTMXEKXVLAXLDKPPFLTQLHS (SEQ ID NO: 31)

VECTTXEKEVLAXLDKAAFLTQHS (SEQ ID NO: 53)

VECTTXEKEVLAXLDKAAF (SEQ ID NO: 54)

VEGTTXEKEVLAXLDKAAF (SEQ ID NO: 55)

and

ECTTXEKEVLAXL (SEQ ID NO 56)

ECTMXEKKVLAXL (SEQ ID NO 57)

wherein the residues which are bold and underlined X carry the stapling and is any amino acid derivative suitable for stapling; and wherein X is any amino acid except M, P and R, with the sequence having optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof.

Preferably, said PKC is selected from the group consisting of an alpha-PKC (αPKC), a beta-PKC (βPKC) including βI and βII PKC, delta-PKC, theta-PKC, eta-PKC and epsilon-PKC. More preferably, said PKC is an αPKC of SEQ ID NO: 1.

In a particular embodiment, the peptide sequence comprises, consists essentially in or consists in

VECTTREKEVLASLDKAAFLTQLHS (SEQ ID NO: 32)

wherein R and S carry the stapling, being preferably 2-(7-octenyl)arginine and 2-(4-pentenyl)serine, respectively;

with the sequence having optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof.

The present invention also relates to a pharmaceutical composition comprising a peptide according to the present disclosure for use for the treatment of diabetes and associated disorders. It further relates to the use of a peptide according to the present disclosure for the manufacture of a drug for the treatment of diabetes and associated disorders.

Optionally, diabetes and associated disorders are selected from the group consisting of type I diabetes, type II diabetes, insulin resistance, diabetic retinopathy, diabetic neuropathy, diabetic nephropathy, hyperglycemia, obesity, hyperinsulinaemia and Bardet Biedl syndrome. Optionally, the peptide is used in combination with one or more additional active drugs preferably selected from the group consisting of an anti-diabetic drug, a hypolipidemic agent, an anti-obesity agent, an anti-hypertensive agent, an anti-steatotic drug, an anti-inflammatory agent, and an agonist of peroxisome proliferator-activator receptors.

BRIEF DESCRIPTION OF THE DRAWINGS

(FIG. 5A) Glucose tolerance: Mice were injected with either vehicle (saline solution), or vehicle+PATAD 417 or vehicle+ADPIF (CPC peptide A-MRO) at day 0. 6 days later (D6) the mice were fasted for 4 hours and at 0 minute received a subcutaneous glucose injection to perform the ipGTT. Glucose levels were measured from tail blood every 30 minutes. Besides the control mice which were fed on chow diet (CTL Chow diet), all the other mice were fed on a high fat/high glucose diet.

(FIG. 5B) Corresponding area under the curve (AUC) for the glucose Tolerance test showed in (A) demonstrating a drop in the AUC in response to the injection of PATAD (PATAD417) and ADPIF (PATAD417-MRP) which shows that ADPIF is more effective than PATAD to reduce the AUC. This indicates that ADPIF is more effective to improve glucose intolerance that PATAD.

(FIG. 6A) Blood glucose excursion curve during ipGTT on day 4 post-PATAS subcutaneous injection (2 mg/kg BW PATAS dosing) in 6-week-old db/db male mice on chow diet Post 8 hours fasting. Glucose bolus (2 g/kg body weight) administered subcutaneously at T=0min and the associated AUC histogram (n=10 mice per group Significance was set at *p-value≤0.05, **p-value≤0.01).

(FIG. 6B) Following 4 weekly PATAS injections, and another 4 weeks without treatment, db/db mice sWAT. Normalized expression levels for the six FATP isoforms (FATP 1-6) in subcutaneous white adipose tissue (sWAT) were determined. n=6 per group with GAPDH as reference gene.

DETAILED DESCRIPTION OF THE INVENTION

Figure 1:
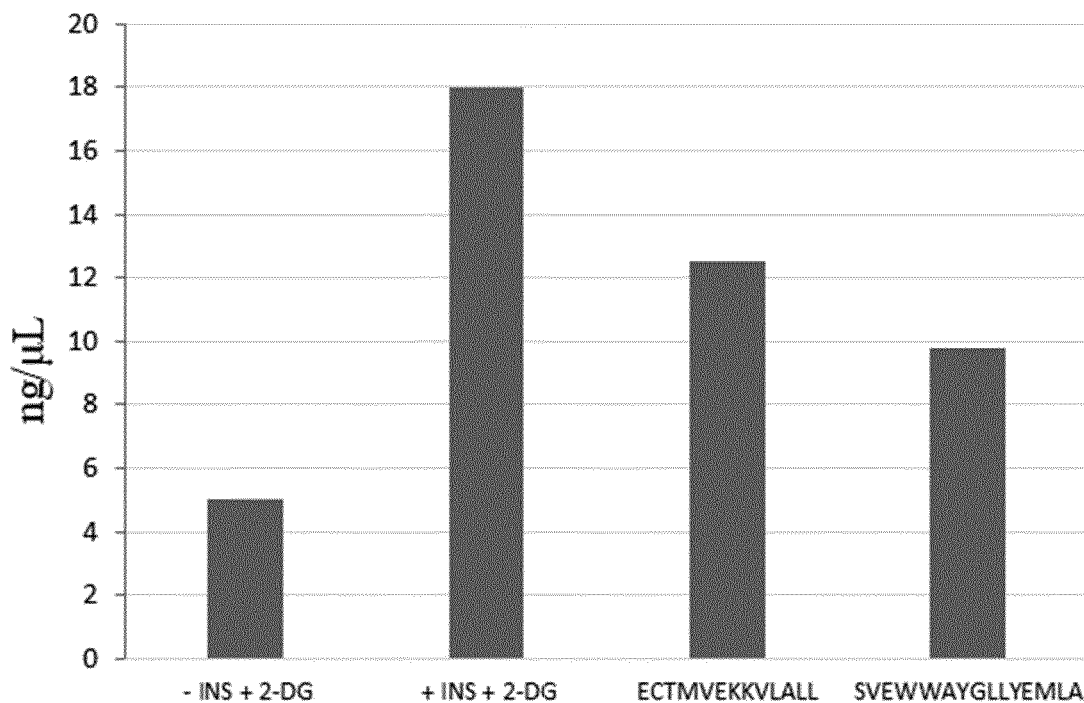
FIG. 1. PKC kinase activity in human adipocytes induced by peptides from alpha PKC. Primary human adipocytes were cultured overnight without insulin and on the next day, the different conditions were used with for each peptide 25 μg of peptide ECTMVEKKVLALL (SEQ ID NO: 50) or 25 ug of peptide SVEWWAYGLLYEMLA (SEQ ID NO: 51) was added to each well and incubated for 30 minutes prior to measuring the PKC activity. Vehicle which is saline solution was the negative control and the positive control used was insulin at 10 mM.

Surprisingly, the inventors provide peptides from the kinase domain of the PKCα and derivatives thereof which specifically decrease the expression of FATP2 (Fatty acid transport protein 2) in adipose tissue. Finally, the peptides are capable of decreasing glycated albumin in plasma, which is biomarker of diabetes.

Therefore, the peptides as described herein are useful for the treatment of diabetes and associated disorders.

Diabetes mellitus is characterized by hyperglycemia. More particularly, type 2 diabetes is characterized by hyperglycemia and insulin resistance. Obesity is thought to be the primary cause of type 2 diabetes in people who are genetically predisposed to the disease. Diabetic retinopathy, diabetic neuropathy, diabetic nephropathy are well-known disorders associated with diabetes and insulin resistance. Then, decreasing the glycemia by increasing the glucose uptake could treat or delay the progression or onset of these diseases.

Accordingly, the invention relates to
- a peptide as defined herein for use for the treatment of diabetes and associated disorders;
- a pharmaceutical composition comprising a peptide as defined herein for use for the treatment of diabetes and associated disorders;
- the use of a peptide or a pharmaceutical composition as defined herein for the manufacture of a medicine for the treatment of diabetes and associated disorders;
- a method for the treatment of diabetes and associated disorders in a subject, comprising administering a therapeutically effective amount of a peptide as defined herein.

Definitions

ALMS1, Alström syndrome protein 1, is a protein encoded by the ALMS1 gene. Mutations in the ALMS1 gene have been found to be causative for Alström syndrome. It is described in several databases, namely UniProt ID No Q8TCU4; Gene ID No 7840, HGNG ID No 428. Reference sequences are disclosed in Genbank under NM_015120.4 for mRNA and NP_055935.4 for protein.

The terms "Protein kinase C" and "PKC" (EC 2.7.11.13) are equivalent and refers to a family of protein kinase enzymes that are involved in controlling the function of other proteins through the phosphorylation of hydroxyl groups of serine and threonine amino acid residues on these proteins. PKC are typically activated by signals such as increases in the concentration of diacylglycerol (DAG) or calcium ions (Ca2+). PKC play important roles in several signal transduction cascades.

The PKC family comprises at least fifteen isozymes in humans, divided into three main subfamilies, conventional (or classical) PKCs, novel PKCs, and atypical PKCs.

Conventional (c)PKCs comprises the isoforms α, βI, βII, and γ. These PKCs require $Ca^{2+}$, DAG, and a phospholipid such as phosphatidylserine for activation.

Novel (n)PKCs include the δ, ε, η, and θ isoforms. These PKCs require DAG, but do not require $Ca^{2+}$ for activation.

Atypical (a)PKCs include the ζ, ι, and λ, isoforms. These PKCs require neither $Ca^{2+}$ nor diacylglycerol for activation.

Protein kinase C alpha type, also called αPKC, PKC-A or PKC-alpha, belongs to a family of serine- and threonine-specific protein kinases that can be activated by calcium and the second messenger diacylglycerol. It is described in several databases, namely UniProt ID No P17252, Gene ID No 9393, HGNG ID No 5578. Reference sequences are disclosed in Genbank under NM_02737.2 for mRNA and NP_002728.1 for protein. The protein sequence of human αPKC is disclosed in SEQ ID NO: 1.

The kinase domain of the αPKC is from position 339 to position 595 as disclosed in SEQ ID NO: 1 and is shown in SEQ ID No 2.

"consists of," "consists essentially of" or "substantially comprises": The description herein of any aspect or embodiment of the invention using terms such as reference to an element or elements is intended to provide support for a similar aspect or embodiment of the invention that "consists of," "consists essentially of" or "substantially comprises" that particular element or elements, unless otherwise stated or clearly contradicted by context. For instance, a peptide or protein described herein as comprising a particular sequence should be understood as also describing a peptide or protein consisting of that sequence, unless otherwise stated or clearly contradicted by context. By "consists essentially of" is intended that the peptide or protein consists of that sequence, but it may also include 1, 2, 3, 4, 5, 6, 7, 8, 9 or 10 substitutions, additions, deletions or a mixture thereof, preferably 1, 2, 3, 4, or 5 substitutions, additions, deletions or a mixture thereof. In particular, by "essentially consist in", it may be intended that the peptide may include 1, 2, 3, 4, 5, 6, 7, 8, 9 or 10 additional amino acids at the N and/or C-terminal end, preferably 1, 2, 3, 4, or 5 additional amino acids, and/or 1, 2 or 3 substitutions, deletions, additions, or a mixture thereof. Preferably, the number of substitutions, additions, deletions or a mixture thereof depends on the length of the sequence. For instance, the percentage of substitutions, deletions, additions, or a mixture thereof may be no more than 30%, preferably no more than 25%.

As used herein, the term "substitution" refers to the exchange of a single amino-acid by another in a peptide sequence.

As used herein, the term "deletion" refers to the removal of a single amino-acid in a peptide sequence.

As used herein, the term "insertion" or "addition" are equivalent and refer to the addition of a single amino-acid in a peptide sequence.

By "substitutions, additions, deletions" is intended a substitution, addition, deletion of one amino acid. Then, when it is refered to "1, 2, 3, 4, 5, 6, 7, 8, 9 or 10 substitutions, additions, deletions or a mixture thereof", "1, 2, 3, 4, or 5 substitutions, additions, deletions or a mixture thereof" or "1, 2 or 3 substitutions, deletions, additions, or a mixture thereof", it means respectively "1, 2, 3, 4, 5, 6, 7, 8, 9 or 10 modification(s) of an amino acid selected from substitutions, additions, deletions and a mixture thereof", "1, 2, 3, 4, or 5 modification(s) of an amino acid selected from substitutions, additions, deletions or a mixture thereof" or "1, 2 or 3 modification(s) of an amino acid selected from substitutions, deletions, additions, or a mixture thereof". "1, 2, 3, 4, or 5 substitutions, additions, deletions or a mixture thereof" also means "from 1 to 5 substitutions, additions, deletions or a mixture thereof". "1, 2, or 3 substitutions, additions, deletions or a mixture thereof" also means "from 1 to 3 substitutions, additions, deletions or a mixture thereof".

In the peptide sequences disclosed herein, the amino acids are represented by their one letter code according to the following nomenclature: A: alanine; C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophane and Y: tyrosine.

As used herein, the terms "sequence identity" or "identity" refers to an exact amino acid to amino acid correspondence of two peptides. Percent of identity can be determined by a direct comparison of the sequence information between two molecules by aligning the sequences, counting the exact number of matches between the two aligned sequences, dividing by the length of the shorter sequence, and multiplying the result by 100.

The sequence identity can be determined by alignment of two peptide sequences using global or local alignment algorithms, depending on the length of the two sequences. Sequences of similar lengths are preferably aligned using global alignment algorithms (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity. GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths.

By "increased", "increase" or "enhance" is intended to refer to a measurement increased by at least 10, 20, 30, 40, 50, 60, 70, 80 or 90% when compared to the measurement measured in absence of the tested molecule in the same conditions. By "decreased" or "decrease" is intended to refer to a measurement decreased by at least 10, 20, 30, 40, 50, 60, 70, 80 or 90% when compared to the measurement measured in absence of the tested molecule in the same conditions.

As used herein, the term "treatment", "treat" or "treating" refers to any act intended to ameliorate the health status of patients, such as cure, alleviate or delay of the disease. It includes preventive as well as therapeutic treatment.

The term treatment designates in particular the correction, retardation, or reduction of an impaired glucose homeostasis. The term "treatment" also designates an improvement in glucose uptake (e.g., capture of glucose by adipocytes). Within the context of the invention, the terms "controlling the blood glucose level" or "the control of blood glucose level" refer to the normalization or the regulation of the blood or plasma glucose level in a mammalian subject having abnormal levels (i.e., levels that are below or above a known reference, median, or average value for a corresponding mammalian subject with a normal glucose homeostasis).

As used herein, the term "effective amount" refers to a quantity of a peptide of the present disclosure or of a pharmaceutical composition of the present disclosure which treats or delays the progression or onset of diabetes or an associated disorder. It can also refer to a quantity of a peptide of the present disclosure or of a pharmaceutical composition of the present disclosure which treats or delays diabetes or an associated disorder.

As used herein, the terms "active principle", "active ingredient" and "active pharmaceutical ingredient" are equivalent and refers to a component of a pharmaceutical composition having a therapeutic effect.

As used herein, the term "therapeutic effect" refers to an effect induced by an active ingredient, such as a peptide of the present disclosure, or by a pharmaceutical composition according to the present disclosure, capable to treat or to delay the progression or onset of diabetes or an associated disorder.

As used herein, the term "excipient or pharmaceutically acceptable carrier" refers to any ingredient except active ingredients that is present in a pharmaceutical composition. Its addition may be aimed to confer a particular consistency or other physical or gustative properties to the final product. An excipient or pharmaceutically acceptable carrier must be devoid of any interaction, in particular chemical, with the active ingredients.

As used herein, the terms "subject", "individual" or "patient" are interchangeable and refer to an animal, preferably to a mammal, even more preferably to a human, including adult, child, newborn and human at the prenatal stage.

In the present document, the term "about" refers to a range of values of ±10% of the specified value. For example, "about 50" comprise values of ±10% of 50, i.e. values in the range between 45 and 55. Preferably, the term "about" refers to a range of values of ±5% of the specified value.

Peptides

The peptide(s) according to the present disclosure present(s) the following features:
  it does not simultaneously comprise one methionine, one proline and one arginine;
  preferably, it adopts a secondary structure which is a helix, preferably an alpha helix;
  it comprises, consists essentially in or consists in a sequence from a segment of the kinase domain of α PKC (Protein Kinase C), preferably a segment of at least 5, 6, 7, 8, 9, 10, 11, 12, 13, 14, 15, 16, 17, 18, 19, 20, 21, 22, 23 or 25 consecutive residues of the kinase domain of α PKC (Protein Kinase C) or a segment from 5 to 40 consecutive residues of the kinase domain of α PKC (Protein Kinase C); and
  the peptide sequence may comprise 1, 2, 3, 4, or 5 amino acid modification(s) selected from substitution(s), deletion(s), addition(s), and a mixture thereof within said sequence of a segment of the kinase domain of the PKC.

The peptide(s) may further present one or several of the following features:
  it has a length of less than 80 amino acids, more preferably less than 60 amino acids, still preferably less than 40 amino acids, and even more preferably less than 30 amino acids;
  it has a length of at least 5 amino acids and less than 40 amino acids, preferably a length of at least 5, 6, 7, 8 or 9 amino acids and less than 30 amino acids, more preferably of at least 5, 6, 7, 8 or 9 amino acids and less than 25 amino acids;
  it is modified by a cross-link;
  it is able to interfere with ALMS1-PKC interaction, in particular to decrease or prevent the interaction between ALMS1 and αPKC; or it is not able to interfere with ALMS1-PKC interaction, in particular to decrease or prevent the interaction between ALMS1 and αPKC;
  it modifies the expression levels of the FATPs expression in adipose tissue, preferentially it decreases the FATP2 expression in adipose tissue.

The peptide(s) may further present one or several of the following features:
  it has a length of less than 80 amino acids, more preferably less than 60 amino acids, still preferably less than 40 amino acids, and even more preferably less than 30 amino acids;
  it has a length of at least 5, 6, 7, 8 or 9 amino acids and less than 40 amino acids, preferably a length of at least 5, 6, 7, 8 or 9 amino acids and less than 30 amino acids, more preferably of at least 5, 6, 7, 8 or 9 amino acids and less than 25 amino acids;
  it is modified by a cross-link;
  it is not able to interfere with ALMS1-PKC interaction, in particular to decrease or prevent the interaction between ALMS1 and αPKC.

In one aspect, the peptide of the present disclosure comprises, consists essentially in or consists in a sequence from a segment of the kinase domain of α PKC (Protein Kinase C). The PKC can be selected from conventional PKC, novel PKC and atypical PKC. In particular, the PKC can be selected from conventional PKC. Preferably, the PKC can be selected from the group consisting of α, βI, βII, and γ PKCs. More preferably, the PKC can be selected from the group consisting of α, βI, and βII PKCs. Even more preferably, the PKC is an α PKC, preferably a human α PKC, more preferably a human αPKC of SEQ ID NO: 1. The kinase domain of the human αPKC is disclosed in SEQ ID NO: 2.

The segment of the kinase domain of α PKC has at least 5, 6, 7, 8, 9, 10, 11, 12, 13, 14, 15, 16, 17, 18, 19, 20, 21, 22, 23 or 25 consecutive residues of the kinase domain of α PKC. In one aspect, the segment of the kinase domain of α PKC has from 5 to 40 consecutive residues of the kinase domain of α PKC (optionally, from 5 to 30 or from 5 to 25 or from 7 to 25 or from 8 to 25 or from 9 to 25 or from 10 to 25 or from 11 to 25 or from 12 to 25).

The kinase domain of PKC from which the segment is selected has preferably at least 40% of identity with the sequence of SEQ ID NO: 2, more preferably at least 45, 50, 55, 60, 65, 70, 75, 80, 85, 90 or 95% of identity with the sequence of SEQ ID NO: 2.

Preferably, said sequence of a segment of the kinase domain of α PKC corresponds to at least 10%, 20%, 30%, 40%, 50%, 60%, 70%, 80%, 90%, 95%, 99% of the sequence of the peptide. In a particular embodiment, the peptide sequence according to the present disclosure consist in the sequence of a segment of SEQ ID NO: 1.

When the segment of the kinase domain of α PKC comprises one methionine and/or one proline and/or one arginine, then the sequence can be modified (i.e., by introducing substitution(s)) so as to remove all the proline residues, and/or all the methionine residues, and/or all the arginine residues. For instance, the sequence can be modified (i.e., by introducing substitution(s)) so as to remove all the proline residues. Alternatively, the sequence can be modified (i.e., by introducing substitution(s)) so as to remove all the methionine residues. Otherwise, the sequence can be modified (i.e., by introducing substitution(s)) so as to remove all the arginine residues. In one aspect, the sequence can be modified (i.e., by introducing substitution(s)) so as to remove all the proline and methionine residues. In another aspect, the sequence can be modified (i.e., by introducing substitution(s)) so as to remove all the proline and arginine residues. In an additional aspect, the sequence can be modified (i.e., by introducing substitution(s)) so as to remove all the methionine and arginine residues. More preferably, the sequence can be modified (i.e., by introducing substitution(s)) so as to remove all the proline residues, all the methionine residues, and all the arginine residues.

Preferably, the peptide comprises no more than 20, preferably no more than 15, more preferably no more than 10, amino acid modifications selected from substitutions, deletions, additions, and a mixture thereof. In a particularly preferred embodiment, the peptide may comprise 1, 2, 3, 4, 5, 6, 7, 8, 9 or 10 amino acid modifications selected from substitution(s), deletion(s), addition(s), and a mixture thereof, preferably 1, 2, 3, 4, or 5, more preferably 1, 2 or 3.

For instance, the peptide has at least 70%, 75%, 80%, 85%, 90%, 95%, 99% of identity with the sequence of a segment of the kinase domain PKC, preferably of SEQ ID No 2. In one embodiment, the part of the sequence of the peptide corresponding to SEQ ID No 2 has at least 70%, 75%, 80%, 85%, 90%, 95%, of identity with the sequence of a segment of SEQ ID No 2.

In a particular aspect, the peptide has at least one amino acid that is substituted, deleted or added in comparison to the sequence of a segment of the kinase domain PKC, preferably of SEQ ID No 2.

For instance, the sequence of a segment of the kinase domain of the PKC may belong to the sequences between positions 339 and 432 of SEQ ID NO: 1, between positions 434 and 544 of SEQ ID NO: 1, between positions 546 and 561 of SEQ ID NO: 1, between positions 563 and 565 of SEQ ID NO: 1, or between positions 568 and 595 of SEQ ID NO: 1.

In one embodiment, the sequence of a segment of the kinase domain of PKC may not include the following residues: G433, E545, S562, S566 of SEQ ID NO: 1.

In one aspect, the peptide of the present disclosure has an alpha helix structure. As used herein, the terms "alpha helix" "α-helix", "classic Pauling-Corey-Branson α-helix" and "3.6$_{13}$-helix" are equivalent and refer to each other. The term "alpha helix" refers to a common motif in the secondary structure of proteins which is a right hand-coiled or spiral conformation (helix) in which every backbone N—H group donates a hydrogen bond to the backbone C=O group of the amino acid located three or four residues earlier along the protein sequence. An alpha helix has an average number of residues per helical turn of about 3.6 residues and 13 atoms are involved in the ring formed by the hydrogen bond.

In a particular embodiment, the peptide of the present disclosure has an alpha helix structure and/or has a sequence which is predictive of an alpha helix structure. Methods to determine the structure of a peptide are well known from the man skilled in the art, such as Circular Dichroism or NMR. Likewise, methods to predict an alpha helix structure of a peptide are well known from the man skilled in the art such as STRIDE (Frishman D., Argos P., Proteins, vol. 23, no 4, 1995, p. 566-579); DEFINE (Richards F. M., Kundrot C. E., Proteins, vol. 3, no 2, 1988, p. 71-84); DSSP (Touw et al. Nucleic Acids Research 2015; 43: D364-D368; Kabsch & Sander. Biopolymers. 1983, 22, 2577-2637).

The alpha helices are located in the kinase domain at the following locations: 372-377; 381-392; 425-432; 437-456; 466-468; 502-504; 507-510; 518-533; 543-552; 563-572; 577-579; 587-593 and 595-597 of SEQ ID NO: 1.

According, the peptide may comprise, consist essentially in or consist in at least one of the following sequences:

```
                                    (SEQ ID NO: 3)
                    VECTMVEKRVLA;

(SEQ ID NO: 4)
                    LMYHIQQV;

LDN;

PDY;

(SEQ ID NO: 5)
                    PEII;

(SEQ ID NO: 6)
                    SVDWWAYGVLLYEMLA;

(SEQ ID NO: 7)
                    EDEDELFQSIME;

PAK;

(SEQ ID NO: 8)
                    GERDVRE;

AFF.
```

In a particular embodiment, the peptide may comprise, consist essentially in or consist in at least one of the following sequences:

```
                                    (SEQ ID NO: 3)
                    VECTMVEKRVLA;
                    and (SEQ ID NO: 8)
                    GERDVRE.
```

Optionally, the peptide may comprise, consist essentially in or consist in at least one of the following sequences: VECTMVEKRVLA (SEQ ID NO: 3); VECTXVEKRVLA (SEQ ID NO: 9); VECTMVEKXVLA (SEQ ID NO: 10); VECTXVEKXVLA (SEQ ID NO: 11); LMYHIQQV (SEQ ID NO: 4); LXYHIQQV (SEQ ID NO: 12); LDN; SVDWWAYGVLLYEMLA (SEQ ID NO: 6); SVDWWAYGVLLYEXLA (SEQ ID NO: 13); SVXWWAYGLLYEMLA (SEQ ID NO: 52); EDEDELFQSIME (SEQ ID NO: 7); EDEDELFQSIXE (SEQ ID NO: 14); GERDVRE (SEQ ID NO: 8); GEXDVRE (SEQ ID NO: 15); GERDVXE (SEQ ID NO: 16); GEXDVXE (SEQ ID NO: 17); LDN; AFF; PDY; XDY; PEII (SEQ ID NO: 5); XEII (SEQ ID NO: 18); PAK; XAK; wherein X is any amino acid except M, P and R. Preferably, X an amino acid favorable to an α-helix secondary structure. For instance, X may be selected from the group consisting of A, D, N, C, G, Q, E, H, L, K, F, S, W and Y, more preferably A, D, N, G, Q, E, H, L, K, F, S, W and Y.

In one aspect, the peptide may comprise, consist essentially in or consist in at least one of the following sequences: VECTMVEKRVLA (SEQ ID NO: 3); VECTXVEKRVLA (SEQ ID NO: 9); VECTMVEKXVLA (SEQ ID NO: 10); VECTXVEKXVLA (SEQ ID NO: 11); LMYHIQQV (SEQ ID NO: 4); LXYHIQQV (SEQ ID NO: 12); SVDWWAYGVLLYEMLA (SEQ ID NO: 6); SVDWWAYGVLLYEXLA (SEQ ID NO: 13); SVXWWAYGLLYEMLA (SEQ ID NO: 52); EDEDELFQSIME (SEQ ID NO: 7); EDEDELFQSIXE (SEQ ID NO: 14); GERDVRE (SEQ ID NO: 8); GEXDVRE (SEQ ID NO: 15); GERDVXE (SEQ ID NO: 16); GEXDVXE (SEQ ID NO: 17); wherein X is any amino acid except M, P and R. In a particular aspect, the peptide can comprise, consist essentially in or consist in VECTMVEKXVLA (SEQ ID NO: 10) with X being K. In another particular aspect, the peptide can comprise, consist essentially in or consist in SVXWWAYGLLYEMLA (SEQ ID NO: 52) with X being E.

In particular, the peptide may comprise, consist essentially in or consist in at least one of the following sequences: VECTMVEKRVLA (SEQ ID NO: 3); VECTXVEKRVLA (SEQ ID NO: 9); VECTMVEKXVLA (SEQ ID NO: 10); VECTXVEKXVLA (SEQ ID NO: 11); LXYHIQQV (SEQ ID NO: 12); SVDWWAYGVLLYEXLA (SEQ ID NO: 13); EDEDELFQSIXE (SEQ ID NO: 14); GERDVRE (SEQ ID NO: 8); GEXDVRE (SEQ ID NO: 15); GERDVXE (SEQ ID NO: 16); GEXDVXE (SEQ ID NO: 17); wherein X is any amino acid except M, P and R. For instance, the peptide may comprise at least one of the following sequences: VECTMVEKRVLA (SEQ ID NO: 3) or VECTTVEKEVLA (SEQ ID NO: 19).

Optionally, the peptide comprises 1, 2, 3, 4, 5, 6, 7, 8, 9, or 10 substitution(s), deletion(s), addition(s), or a mixture thereof, preferably, 1, 2, 3, 4, or 5 substitution(s), deletion(s), addition(s), or a mixture thereof, more preferably, 1, 2, or 3 substitution(s).

Optionally, the peptide may comprise, consist essentially in or consist in at least one of the following sequences: VECTMVEKRVLA (SEQ ID NO: 3) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; VECTXVEKRVLA (SEQ ID NO: 9) with optionally modification(s) of an amino acid selected from 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; VECTMVEKXVLA (SEQ ID NO: 10) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; VECTXVEKXVLA (SEQ ID NO: 11) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; LMYHIQQV (SEQ ID NO: 4) with optionally 1, 2, or 3 modification(s) of an amino acid selected from substitution(s) deletion(s), addition(s), and a mixture thereof; LXYHIQQV (SEQ ID NO: 12) with optionally 1, 2, or 3 modification(s) of an amino acid selected from substitution(s) deletion(s), addition(s), and a mixture thereof; LDN; SVDWWAYGVLLYEMLA (SEQ ID NO: 6) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; SVDWWAYGVLLYEXLA (SEQ ID NO: 13) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; SVXWWAYGLLYEMLA (SEQ ID NO: 52) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; EDEDELFQSIME (SEQ ID NO: 7) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; EDEDELFQSIXE (SEQ ID NO: 14) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; GERDVRE (SEQ ID NO: 8) with optionally 1, 2, or 3 modification(s) of an amino acid selected from substitution(s) deletion(s), addition(s), and a mixture thereof; GEXDVRE (SEQ ID NO: 15) with optionally 1, 2, or 3 modification(s) of an amino acid selected from substitution(s) deletion(s), addition(s), and a mixture thereof; GERDVXE (SEQ ID NO: 16) with optionally 1, 2, or 3 modification(s) of an amino acid selected from substitution(s) deletion(s), addition(s), and a mixture thereof; GEXDVXE (SEQ ID NO: 17) with optionally 1, 2, or 3 modification(s) of an amino acid selected from substitution(s) deletion(s), addition(s), and a mixture thereof; LDN; AFF; PDY; XDY; PEII (SEQ ID NO: 5); XEII (SEQ ID NO: 18); PAK; XAK; wherein X is any amino acid except M, P and R. Preferably, X an amino acid favorable to an α-helix secondary structure. For instance, X may be selected from the group consisting of A, D, N, C, G, Q, E, H, L, K, F, S, W and Y, more preferably A, D, N, G, Q, E, H, L, K, F, S, W and Y.

In one aspect, the peptide may comprise, consist essentially in or consist in at least one of the following sequences: VECTMVEKRVLA (SEQ ID NO: 3) with optionally 1, 2, or 3 modification(s) of an amino acid selected from substitution(s) deletion(s), addition(s), and a mixture thereof; VECTXVEKRVLA (SEQ ID NO: 9) with optionally modification(s) of an amino acid selected from 1, 2, or 3 modification(s) of an amino acid selected from substitution(s) deletion(s), addition(s), and a mixture thereof; VECTMVEKXVLA (SEQ ID NO: 10) with optionally 1, 2, or 3 modification(s) of an amino acid selected from substitution(s) deletion(s), addition(s), and a mixture thereof; VECTXVEKXVLA (SEQ ID NO: 11) with optionally 1, 2, or 3 modification(s) of an amino acid selected from substitution(s) deletion(s), addition(s), and a mixture thereof; LMYHIQQV (SEQ ID NO: 4) with optionally 1, 2, or 3 modification(s) of an amino acid selected from substitution(s) deletion(s), addition(s), and a mixture thereof; LXYHIQQV (SEQ ID NO: 12) with optionally 1, 2, or 3 modification(s) of an amino acid selected from substitution(s) deletion(s), addition(s), and a mixture thereof; SVDWWAYGVLLYEMLA (SEQ ID NO: 6) with optionally 1, 2, or 3 modification(s) of an amino acid selected from substitution(s) deletion(s), addition(s), and a mixture thereof; SVDWWAYGVLLYEXLA (SEQ ID NO: 13) with optionally 1, 2, or 3 modification(s) of an amino acid selected from substitution(s) deletion(s), addition(s), and a mixture thereof; SVXWWAYGLLYEMLA (SEQ ID NO: 52) with optionally 1, 2, or 3 modification(s) of an amino acid selected from substitution(s) deletion(s), addition(s), and a mixture thereof; EDEDELFQSIME (SEQ ID NO: 7) with optionally 1, 2, or 3 modification(s) of an amino acid selected from substitution(s) deletion(s), addition(s), and a mixture thereof; EDEDELFQSIXE (SEQ ID NO: 14) with optionally 1, 2, or 3 modification(s) of an amino acid selected from substitution(s) deletion(s), addition(s), and a mixture thereof; GERDVRE (SEQ ID NO: 8) with optionally 1, 2, or 3 modification(s) of an amino acid selected from substitution(s) deletion(s), addition(s), and a mixture thereof; GEXDVRE (SEQ ID NO: 15) with optionally 1, 2, or 3 modification(s) of an amino acid selected from substitution(s) deletion(s), addition(s), and a mixture thereof; GERDVXE (SEQ ID NO: 16) with optionally 1, 2, or 3 modification(s) of an amino acid selected from substitution(s) deletion(s), addition(s), and a mixture thereof; GEXDVXE (SEQ ID NO: 17) with optionally 1, 2, or 3 modification(s) of an amino acid selected from substitution(s) deletion(s), addition(s), and a mixture thereof; wherein X is any amino acid except M, P and R. Preferably, X an amino acid favorable to an α-helix secondary structure. For instance, X may be selected from the group consisting of A, D, N, C, G, Q, E, H, L, K, F, S, W and Y, more preferably A, D, N, G, Q, E, H, L, K, F, S, W and Y.

In particular, the peptide may comprise, consist essentially in or consist in at least one of the following sequences: VECTMVEKRVLA (SEQ ID NO: 3) with optionally 1, 2, or 3 modification(s) of an amino acid selected from substitution(s) deletion(s), addition(s), and a mixture thereof; VECTXVEKRVLA (SEQ ID NO: 9) with optionally modification(s) of an amino acid selected from 1, 2, or 3 modification(s) of an amino acid selected from substitution(s) deletion(s), addition(s), and a mixture thereof; VECTMVEKXVLA (SEQ ID NO: 10) with optionally 1, 2, or 3 modification(s) of an amino acid selected from substitution(s) deletion(s), addition(s), and a mixture thereof; VECTXVEKXVLA (SEQ ID NO: 11) with optionally 1, 2, or 3 modification(s) of an amino acid selected from substitution(s) deletion(s), addition(s), and a mixture thereof; GERDVRE (SEQ ID NO: 8) with optionally 1, 2, or 3 modification(s) of an amino acid selected from substitution(s) deletion(s), addition(s), and a mixture thereof; GEXDVRE (SEQ ID NO: 15) with optionally 1, 2, or 3 modification(s) of an amino acid selected from substitution(s) deletion(s), addition(s), and a mixture thereof; GERDVXE (SEQ ID NO: 16) with optionally 1, 2, or 3 modification(s) of an amino acid selected from substitution(s) deletion(s), addition(s), and a mixture thereof; GEXDVXE (SEQ ID NO: 17) with optionally 1, 2, or 3 modification(s) of an amino acid selected from substitution(s) deletion(s), addition(s), and a mixture thereof; wherein X is any amino acid except M, P and R. Preferably, X an amino acid favorable to an α-helix secondary structure. For instance, X may be selected from the group consisting of A, D, N, C, G, Q, E, H, L, K, F, S, W and Y, more preferably A, D, N, G, Q, E, H, L, K, F, S, W and Y.

For instance, the peptide may comprise at least one of the following sequences: VECTMVEKRVLA (SEQ ID NO: 3) or VECTTVEKEVLA (SEQ ID NO: 19).

In one aspect, the peptide may comprise, consist essentially in or consist in at least one of the following sequences:

a) VECTXVEKXVLALLDKXXFLTQLHS (SEQ ID NO: 20) wherein X is any amino acid except M, P and R, preferably, an amino acid favorable to an α-helix secondary structure, more preferably selected from the group consisting of A, D, N, C, G, Q, E, H, L, K, F, S, W and Y, still more preferably A, D, N, G, Q, E, H, L, K, F, S, W and Y, with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof;

b) VECTMVEKRVLALLDKXXFLTQLHS (SEQ ID NO: 21) wherein X is any amino acid except M, P and R, preferably, an amino acid favorable to an α-helix secondary structure, more preferably selected from the group consisting of A, D, N, C, G, Q, E, H, L, K, F, S, W and Y, still more preferably A, D, N, G, Q, E, H, L, K, F, S, W and Y, with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof;

c) VECTXVEKRVLALLDKPPFLTQLHS (SEQ ID NO: 22) wherein X is any amino acid except M, P and R, preferably, an amino acid favorable to an α-helix secondary structure, more preferably selected from the group consisting of A, D, N, C, G, Q, E, H, L, K, F, S, W and Y, still more preferably A, D, N, G, Q, E, H, L, K, F, S, W and Y, with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof;

d) VECTMVEKXVLALLDKPPFLTQLHS (SEQ ID NO: 23) wherein X is any amino acid except M, P and R, preferably, an amino acid favorable to an α-helix secondary structure, more preferably selected from the group consisting of A, D, N, C, G, Q, E, H, L, K, F, S, W and Y, still more preferably A, D, N, G, Q, E, H, L, K, F, S, W and Y, with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof;

and the sequence of any segment of at least 5, 6, 7, 8, 9, 10, 11, 12, 13, 14, 15, 16, 17, 18, 19, 20, 21, 22, 23 or 25 consecutive residues of any sequence a) to d).

In another particular embodiment, the peptide according to the present disclosure is designed or modified in order to maintain it in an alpha helical conformation. As known in the art, this can be achieved via a variety of methods, including modification of the amino acid sequence with substitution of amino acids not critical for biological effects, use of non-natural amino acids, peptide cyclization, and modifications to the peptide backbone or addition of chemical links between amino acids in the peptide chain. Such modifications can be made to peptides, for example, to increase their thermal and protease stability.

In particular, the peptide of the present disclosure is modified by a chemical cross-link. For instance, the peptide can be a stapled peptide. In one embodiment, the peptide of the present disclosure is stapled. The term "stapled peptide" or "stitched peptide", as used herein, refers to an artificially modified peptide in which the peptide secondary structure is stabilized with one or more artificial molecular crosslinks (bridges) that connect adjacent turns of α-helices in the peptide. The methods for preparing stapled peptides are well known in the art, for instance in Verdine & Hilinski (2012, Methods Enzymol, 503, 3-33), WO10033617 and WO10011313, the disclosure of which is incorporated herein by reference.

In one embodiment, the crosslinks of the stapled peptide of the present disclosure are i+3, and/or i+4, and/or i+7 crosslinks. In a peptide, a "i+3 crosslink" is a crosslink between an amino acid, the "i" amino acid, and another amino acid present at a distance of 3 amino acid residues from the i amino acid. In a peptide, a "i+4 crosslink" is a crosslink between an amino acid, the "i" amino acid, and another amino acid present at a distance of 4 amino acid residues from the i amino acid. In a peptide, a "i+7 crosslink" is a crosslink between an amino acid, the "i" amino acid, and another amino acid present at a distance of 7 amino acid residues from the i amino acid. In a preferred aspect, the peptide has a "i+7 crosslink". For the shortest sequences, in particular those including three to four residues, the crosslink is i+3 and i+4 and it is introduced between residues which are outside of this sequence. When the sequences are long enough, the cross-link of i+7 is preferred.

To illustrate this aspect on one particular peptide, the peptide may comprise, consist essentially in or consist in one of the following sequences:

```
                                          (SEQ ID NO: 24)
VECTMXEKRVLAX (SEQ ID NO: 25)
VECTXXEKRVLAX (SEQ ID NO: 26)
VECTMXEKXVLAX (SEQ ID NO: 27)
VECTXXEKXVLAX (SEQ ID NO: 28)
VECTXXEKXVLAXLDKXXFLTQLHS (SEQ ID NO: 29)
VECTMXEKRVLAXLDKXXFLTQLHS (SEQ ID NO: 30)
VECTXXEKRVLAXLDKPPFLTQLHS (SEQ ID NO: 31)
VECTMXEKXVLAXLDKPPFLTQLHS (SEQ ID NO: 53)
VECTTXEKEVLAXLDKAAFLTQHS (SEQ ID NO: 54)
VECTTXEKEVLAXLDKAAF (SEQ ID NO: 55)
VEGTTXEKEVLAXLDKAAF
and (SEQ ID NO 56)
ECTTXEKEVLAXL (SEQ ID NO 57)
ECTMXEKKVLAXL
``` wherein the residues which are bold and underlined X carry the stapling and is any amino acid derivative suitable for stapling; and wherein X is any amino acid except M, P and R, preferably, an amino acid favorable to an α-helix secondary structure, more preferably selected from the group consisting of A, D, N, C, G, Q, E, H, L, K, F, S, W and Y, still more preferably A, D, N, G, Q, E, H, L, K, F, S, W and Y, and with the sequence having optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof.

For instance, in the context of a i+7 stapling, the first X is a 2-(7-octenyl)amino acid (for instance a 2-(7-octenyl) alanine or a 2-(7-octenyl)arginine) and the second X is a 2-(4-pentenyl)amino acid (for instance a 2-(4-pentenyl)alanine or a 2-(4-pentenyl)serine). Specific combinations can 2-(7-octenyl)alanine and 2-(4-pentenyl)alanine; 2-(7-octenyl)alanine and 2-(4-pentenyl)serine; 2-(7-octenyl)arginine and 2-(4-pentenyl)alanine; or 2-(7-octenyl)arginine and 2-(4-pentenyl)serine.

In a particular embodiment, the peptide can be

```
                                          (SEQ ID NO: 32)
VECTTREKEVLASLDKAAFLTQLHS
``` wherein R and S carry the stapling, being preferably 2-(7-octenyl)arginine and 2-(4-pentenyl)serine, respectively;

with the sequence having optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof.

In a particular embodiment, the peptide according to the present disclosure is a cyclic peptide. As used herein, the term "cyclic peptide" or "circular peptide" are equivalent and refers to a peptide in which the N-terminus and the C-terminus, or the N-terminus and the side chain of another amino acid, preferably the C-terminal amino acid, or the C-terminus and the side chain of another amino acid, preferably the N-terminal amino acid, or the side chain of an amino acid and the side chain of another amino acid, preferably the N-terminal amino acid and the C-terminal amino acid, are linked with a covalent bond that generates a ring structure. As used herein, the term "N-terminus", "amino-terminus", "NH2-terminus", "N-terminal end" and "amine-terminus" are equivalent and refer to the free amine group (—NH2) present on the first amino acid of the peptide. As used herein, the term "C-terminus", "carboxyl-terminus", "carboxy-terminus", "C-terminal end", and "COOH-terminus" are equivalent and refer to the free carboxyl group (—COOH) present on the last amino acid of the peptide.

In one embodiment, the peptide according to the present disclosure has a length of less than 80 amino acids, more preferably less than 60 amino acids, still preferably less than 40 amino acids, and even more preferably less than 30 amino acids. In a particular embodiment, the peptide according to the present disclosure has a length of less than 25 amino acids. In another particular embodiment, the peptide according to the present disclosure has a length of less than 20 amino acids, preferably of less than 15 amino acids. Preferably, the peptide has a minimum length greater than 4, 5, 6, 7, 8, 9, 10, 11, 12, 13, 14, 15, 16, 17, 18, 19, or 20 amino acids. For instance, the peptide has a length of at least 4 amino acids and less than 40 amino acids, preferably a length of at least 4 amino acids and less than 30 amino acids; more preferably of at least 6 amino acids and less than 25 amino acids.

In one embodiment, the peptide according to the present disclosure is capable of interfering with ALMS1-PKC interaction, in particular to decrease or prevent the interaction between ALMS1 and αPKC. In other words, the peptide according to the present disclosure is capable of blocking the interaction between ALMS1 and αPKC. Alternatively, the peptide according to the present disclosure is not capable of interfering with ALMS1-PKC interaction, in particular to decrease or prevent the interaction between ALMS1 and αPKC. In other words, the peptide according to the present disclosure is not capable of blocking the interaction between ALMS1 and αPKC.

In order to determine the effect of a peptide on the binding of αPKC to ALMS1, any technology known by the person skilled in the art can be carried out, in particular any method suitable for determining protein interactions. For example, recombinant or purified native ALMS1 or αPKC can be bound to a surface plasmon resonance ship and the other molecule flowed over the chip to assess the binding affinity, for example in a Biacore (General Electric, USA) machine.

The effect of peptide(s) on the binding of αPKC to ALMS1 is determining by measuring the binding of αPKC to ALMS1 in absence and in presence of the tested peptide(s) and by comparing the bindings of αPKC to ALMS1.

In particular, immunoprecipitation assay using ALMS1 as bait can be carried. The assay can be carried out with cells, in particular adipocytes, cultured in absence and/or presence of insulin, preferably in absence of insulin. The peptides to be tested are added in the culture medium. Then, αPKC is immunodetected.

By "decreased", "decrease" or "prevent" is intended to refer to a binding decreased by at least 10, 20, 30, 40, 50, 60, 70, 80 or 90% when compared to the binding measured in absence of the tested molecule in the same conditions.

In one embodiment, the peptide according to the present disclosure is capable of decreasing the expression of FATP2 in adipose tissue.

FATP2 is also called Solute Carrier Family 27 Member 2 (SLC27A2). This protein is disclosed in the database UniProtKB under 014975. The gene is described in UniGene database under Hs.11729. Sequences of reference can be found in NCBI under NP_003636.2 and NM_003645.3 for the isoform 1 and under NP_001153101.1 and NM_001159629.1. for the isoform 2.

By "decreased" or "decrease" is intended to refer to an expression decreased by at least 10, 20, 30, 40, 50, 60, 70, 80 or 90% when compared to the expression measured in absence of the peptide in the same conditions. The expression can be measured either at the protein level (e.g., with antibodies) or at the mRNA level.

The expression can be measured at the protein level by any available method such as immuno-histochemistry, semi-quantitative Western-blot or by protein or antibody arrays. Antibodies directed to FATP2 are commercially available, for instance from Origene, ref TA350424 or TA333990; or Santa Cruz Biotechnology, ref sc-393906.

The expression can also be measured at the mRNA level by any available method. Preferably, the expression level of FATP2 is determined by measuring the quantity of the mRNA transcripts by quantitative RT-PCR, real time quantitative RT-PCR, Nanostring technology PCR or by high-throughput sequencing technology such as RNA-Seq or sequencing technologies using microfluidic systems. More specifically, the expression is measured by the method specified in the Example section.

In a particular embodiment, the effect on the FATP2 expression caused by the peptide in the adipose tissue is preferably specific to FATP2. In this embodiment, the peptide can have no or less effect on the expression of the other FATPs, i.e. FATP1, FATP3, FATP4, FATP5 and FATP6, in the adipose tissue, in particular of a mammal.

In a particular embodiment, the peptide according to the present disclosure presents the following features
it does not simultaneously comprise one methionine, one proline and one arginine;
it adopts a secondary structure which is a helix, preferably an alpha helix; and
it comprises, consists essentially in or consists in a sequence from a segment of the kinase domain of α PKC (Protein Kinase C).
and further present one, two, three, four or all following features:
it modifies the expression levels of the FATPs expression in adipose tissue, preferentially it decreases the FATP2 expression in adipose tissue;
it has a length of at least 4 amino acids and less than 40 amino acids, preferably a length of at least 4 amino acids and less than 30 amino acids, more preferably of at least 4 amino acids and less than 25 amino acids;
it adopts a secondary structure which is a helix, preferably an alpha helix;
it is modified by a cross-link.

In a more specific embodiment, the peptide according to the present disclosure presents the following features:
it does not simultaneously comprise one methionine, one proline and one arginine;
it has a length of at least 4 amino acids and less than 40 amino acids, preferably a length of at least 4 amino acids and less than 30 amino acids, more preferably of at least 4 amino acids and less than 25 amino acids;
it adopts a secondary structure which is a helix, preferably an alpha helix.

In another more specific embodiment, the peptide according to the present disclosure presents the following features:
it decreases the FATP2 expression in adipose tissue;
it does not simultaneously comprise one methionine, one proline and one arginine;
it has a length of at least 4 amino acids and less than 40 amino acids, preferably a length of at least 4 amino acids and less than 30 amino acids, more preferably of at least 4 amino acids and less than 25 amino acids;
it adopts a secondary structure which is a helix, preferably an alpha helix.

The peptide according to the present disclosure may further comprise a moiety facilitating its cellular uptake or entry, in particular a PTD (protein transduction domain). PTD generally comprises a certain amino acid sequence of 10 to 20 amino acids (Matsushita and Matsui, (2005), J Mol Med 83, 324-328; Vivès et al, Biochimic et Biophysica Acta, 2008, 1786, 126-138). PTD is mainly composed of basic amino acids such as arginine or lysine, and representative examples of the PTD include arginine rich peptides such as poly $R_8$ (RRRRRRRR (SEQ ID NO: 33)) or (RRPRRPRR-PRRPRRP (SEQ ID NO: 34)), antennapedia or penetratin peptide such as (RQIKIWFQNRRMKWKK (SEQ ID NO: 35)) or HIV-Tat (YGRKKRRQRRR (SEQ ID NO: 36)).

The peptide according to the present disclosure can be made of natural amino acids and/or unnatural amino acids. The term "unnatural amino acids" is defined as an analog or derivative of a natural amino acid (i.e., Alanine, Valine, Glycine, Leucine, Isoleucine, Lysine, Arginine, Glutamic acid, Glutamine, Aspartic acid, Asparagine, Histidine, Tyrosine, Phenylalanine, Tryptophan, Serine, Proline, Threonine, Cysteine, Methionine). They present a modified side chain, e.g. shorter, longer or with different functional groups. Isomers D and
L are contemplated, in particular because isomers D are not sensible to proteases. In addition, modifications in some or all peptide bounds are also contemplated in order to increase the proteolysis resistance, in particular by (—CO—NH—) by (—CH$_2$—NH—), (—NH—CO—), (—CH$_2$—O—), (—CH$_2$—S—), (—CH$_2$—CH$_2$—), (—CO—CH$_2$—), (—CHOH—CH$_2$—), (—N═N—), and/or (—CH═CH—). The peptide can present a carboxylic C terminal end (—COO$^-$) and an amide one (—CONH$_2$). The peptide can also be D-retro-inverso sequence of a peptide as disclosed herein. The N terminal can be modified, especially with an acetyl radical.

Optionally, the peptide can be PEGylated in order to increase its stability. Further optionally the peptide can be formulated in non-aqueous protic solvent solutions such as propylene glycol and polyethylene glycol. The peptide may also be packaged into poly lactic co-glycolic acid microsphere depot formulation. Many sustained-release delivery systems exist, and many of these are appropriate for use in the present disclosure. For example, polymer-based slow-release compositions based upon degradable polymers such as PLGA, poly-lactate or poly-glycolate are suitable, as are lipid-based depot compositions, such as those described in WO2005/117830 and/or WO2006/075124, the complete disclosures of which are being hereby incorporated by reference. The formulation of active agents into biodegradable polymer depot formulations is well established and well known in the art, and the peptides of the present disclosure may thus be formulated with these using known methods. Preferably, the composition of the present disclosure is capable of releasing the peptide at a functional concentration for at least 1 month.

By "a peptide" is intended to refer to a peptide as disclosed above or a combination of different peptides as disclosed above. For instance, 2, 3, 4, 5 or 6 different peptides can be used, preferably 2 or 3, more preferably 2.

Combinations

The peptide(s) according to the present disclosure can be used in combination with one or more additional active drugs, for instance an anti-diabetic drug, a hypolipidemic agent, an anti-obesity agent, an anti-hypertensive agent, an anti-steatotic drug, an anti-inflammatory agent, and an agonist of peroxisome proliferator-activator receptors.

Accordingly, the present invention relates to:
 a peptide or a pharmaceutical composition comprising a peptide as disclosed herein for use in the treatment of diabetes and associated disorders, in combination with one or more additional active drugs, in particular as disclosed herein;
 a pharmaceutical composition comprising a peptide as disclosed herein and one or more additional active drugs for use in the treatment of diabetes and associated disorders;
 a product, combined preparation or kit comprising a peptide according to the present disclosure and one or more additional active drugs, in particular as disclosed herein, for simultaneous, separate or sequential use in the treatment of diabetes and associated disorders;
 the use of a peptide for the manufacture of a medicine for the treatment of diabetes and associated disorders in combination with one or more additional active drugs;
 the use of a peptide as disclosed herein and one or more additional active drugs, in particular as disclosed herein, for the manufacture of a medicine for the treatment of diabetes and associated disorders;
 a method for the treatment of diabetes and associated disorders in a subject, comprising administering a therapeutically effective amount of a peptide as disclosed herein and a therapeutically effective amount of one or more additional active drugs;
 a method for the treatment of diabetes and associated disorders in a subject, comprising administering a therapeutically effective amount of a pharmaceutical composition comprising a peptide as disclosed herein and one or more additional active drugs, in particular as disclosed herein.

In particular, a therapeutic or sub-therapeutic effective amount of one or more additional active drugs can be used. By "sub-therapeutic" is intended to refer to an amount that can be for instance 90, 80, 70, 60, 50, 40, 30, 20 or 10% of the conventional therapeutic dosage (in particular for the same indication and/or the same administration route and/or frequency of administration).

The anti-diabetic drug can be for instance insulin, insulin derivatives and mimetics; insulin secretagogues such as the sulfonylureas (e.g., chlorpropamide, tolazamide, acetohexamide, tolbutamide, glyburide, glimepiride, glipizide); gliflozins such as emplagliflozin and dapagliflozin; glyburide and Amaryl; liraglutide (NN2211); insulinotropic sulfonylurea receptor ligands such as meglitinides, e.g. nateglinide and repaglinide; thiazolidinediones (e.g., rosiglitazone (AVANDIA), troglitazone (REZULIN), pioglitazone (ACTOS), balaglitazone, rivoglitazone, netoglitazone, troglitazone, englitazone, ciglitazone, adaglitazone, darglitazone that enhance insulin action (e.g., by insulin sensitization), thus promoting glucose utilization in peripheral tissues; protein tyrosine phosphatase-IB (PTP-1B) inhibitors such as PTP-112; Cholesteryl ester transfer protein (CETP) inhibitors such as torcetrapib, GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose cotransporter inhibitors such as T-1095 or canagliflozin; glycogen phosphorylase A inhibitors such as BAY R3401; biguanides such as metformin and other agents that act by promoting glucose utilization, reducing hepatic glucose production and/or diminishing intestinal glucose output; alpha-glucosidase inhibitors such as acarbose and migiitoi) and other agents that slow down carbohydrate digestion and consequently absorption from the gut and reduce postprandial hyperglycemia; GLP-1 (glucagon like peptide-1), GLP-1 analogs such as Exendin-4 and GLP-1 mimetics; and DPPIV (dipeptidyl peptidase IV) inhibitors such as vildagliptin. It can also be an anti-diabetic drug described in Expert Opin Investig Drugs 2003, 12(4): 623-633, FIGS. 1 to 7. Antidiabetic drug may also include a molecule preventing the binding of αPKC and ALMS1 such as those disclosed in WO 2015/114062, the disclosure thereof being incorporated herein by reference.

The hypolipidemic agent can be for instance 3-hydroxy-3-methyl-glutaryl coenzyme A (HMG-CoA) reductase inhibitors, e.g. lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands such as obeticholic acid; bile acid sequestrants, such as cholestyramine and colesevelam; fibrates; nicotinic acid and aspirin; aramchol, a transmembrane G protein-coupled receptor (TGR) 5 agonist.

The anti-obesity agent can be for instance orlistat, rimonabant, phentermine, topiramate, qnexa, and locaserin.

The anti-hypertensive agent can be for instance loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors such as sacubitril; ACE/NEP inhibitors such as omapatrilat, sampatrilat and fasidotril; angiotensin II antagonists such as candesartan, eprosartan, irbesartan, losartan, telmisartan and valsartan, in particular valsartan; combinations of NEP inhibitors and angiotensin II antagonists such as sacubitril and valsartan (i.e. Entresto); renin inhibitors such as ditekiren, zankiren, terlakiren, aliskiren, RO 66-1132 and RO-66-1168; beta-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

The agonist of peroxisome proliferator-activator receptors can be for instance fenofibrate, pioglitazone, rosiglitazone, tesaglitazar, BMS-298585, L-796449, the compounds specifically described in the patent application WO 2004/103995 i.e. compounds of examples 1 to 35 or compounds specifically listed in claim 21, or the compounds specifically described in the patent application WO 03/043985 i.e. compounds of examples 1 to 7 or compounds specifically listed in claim 19 and especially (R)-1-{4-[5-methyl-2-(4-trifluoromethyl-phenyl)-oxazol-4-ylmethoxy]-benzenesulfonyl}-2,3-dihy dro-1H-indole-2-carboxylic or a salt thereof.

Other drugs of interest can be for instance cenicriviroc, simtuzumab, selonsertib, emricasan. In a particular embodiment, the one or more additional active drugs used in combination with the peptide can be selected among: a GLP-1 analog such as liraglutide, obeticholic acid, a gliflozin, simtuzumab (GS 6624), cenicriviroc, aramchol, a Galectin 3 inhibitor such as GR-MD-02, a TGR5 agonist and a dual FXR/TGR5 agonist such as INT-777 or INT-767, and emricasan.

The anti-inflammatory agent can be any drug known by the skilled person such as nonsteroidal anti-inflammatory agents (NSAIDs), including salicylic acid, ibuprofen in its various forms and naproxen in its various forms, a steroidal anti-inflammatory such as corticosteroids, an anti-inflammatory anti-TNF alpha antibody and combinations thereof.

The form of the pharmaceutical compositions, the route of administration, the dosage and the regimen naturally depend upon the condition to be treated, the severity of the illness, the age, weight, and sex of the patient, etc.

The pharmaceutical or therapeutic compositions of the present disclosure can be formulated for a topical, oral, parenteral, intranasal, intravenous, intramuscular, subcutaneous or intraocular administration and the like.

The peptide used in the pharmaceutical composition of the present disclosure is present in a therapeutically effective amount.

The pharmaceutical composition comprising the peptide is formulated in accordance with standard pharmaceutical practice (Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

In one aspect, the present invention provides a stable formulation for parenteral injection of the pharmaceutical composition according to the present disclosure comprising a peptide or a salt thereof, wherein the peptide has been dried and then is reconstituted in a solvent prior to use. The peptide (or, in embodiments where the formulation comprises two or more peptides, each of the peptides) is mixed with a non-volatile buffer and dried to a dry peptide powder. Suitable buffers include, but are not limited to, glycine buffers, citrate buffers, phosphate buffers, and mixtures thereof. In one embodiment, the buffer is a glycine buffer.

In another embodiment, the buffer is a mixture of citrate buffer and phosphate buffer. In some embodiments, wherein the formulation comprises two or more peptides, the first and second buffer are the same. In some embodiments, wherein the formulation comprises two or more peptides, the first and the second buffer are different. Alternatively, the pharmaceutical composition according to the present disclosure may be stored in an aqueous state. The solution may contain, if desired, further additives or excipients, which must be compatible with the active principle and, if they are not removed during the freeze-drying stage, they must also be compatible with the route of administration. For parenteral administration, the composition may be injected intradermally, subcutaneously, intramuscularly, or intravenously. Preferably, the composition or peptide is injected or to be injected subcutaneously, in particular in the fat tissue.

It may preferably be placed with a mini-osmotic pump or other controlled delivery device implanted into the body. Preferably, it may be mixed with other compounds to make a depot slow release formulation. A preferred route of administration is subcutaneous injection, for instance by using a disposable or multiunit dispensing device, similar to an insulin pen. The peptide can also be administered by a device allowing the subcutaneous administration without any needle, a non-invasive system.

In addition, the peptide can be administered by using any drug delivery system available. In particular, the use of recombinant human hyaluronidase enzyme, rHuPH20, to enable and optimize subcutaneous drug delivery for appropriate co-administered therapies is contemplated.

With the technology, some biologics and compounds that are administered intravenously may instead be delivered subcutaneously, or under the skin, potentially providing a better experience for patients, and increasing health system efficiency by reducing administration time, injection pain and infusion site reactions.

In one embodiment, the peptide of the present disclosure may be mixed with other compounds to make a depot slow release formulation. This may then be injected subcutaneously to form a slow release depot.

For oral administration, the composition can be formulated into conventional oral dosage forms such as tablets, capsules, powders, granules and liquid preparations such as syrups, elixirs, and concentrated drops. Non-toxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials, are also necessary. For example, starch, gelatine, sugars such as lactose or dextrose, and natural or synthetic gums can be used as binders. Disintegrants are also necessary in the tablets to facilitate break-up of the tablet. Disintegrants include starches, clays, celluloses, algins, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, intrapulmonary inhalation, rectal or vaginal suppositories can be used. In one embodiment, the invention may be administered by the intrapulmonary route using either a dry powder or liquid formulation administered using an intrapulmonary drug delivery device according to methods known in the art. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Pharmaceutical compositions according to the present disclosure may be formulated to release the active drug substantially immediately upon administration or at any predetermined time or time period after administration.

Pharmaceutical compositions according to the present disclosure can comprise one or more peptides of the present disclosure associated with pharmaceutically acceptable excipients and/or carriers. These excipients and/or carriers are chosen according to the form of administration as described above.

In a particular embodiment, the pharmaceutical composition according to the present disclosure comprises between 0.01 ng and 10 g of the peptide of the present disclosure. In one embodiment, pharmaceutical composition according to the present disclosure comprises between 0.1 ng and 1 g of the peptide of the present disclosure.

All the references cited in this application, including scientific articles and summaries, published patent applications, granted patents or any other reference, are entirely incorporated herein by reference, which includes all the results, tables, figures and texts of theses references.

Although having different meanings, the terms "comprising", "having", "consisting in" and "containing" can be replaced one for the other in the entire application.

Further aspects and advantages of the present disclosure will be described in the following examples, which should be regarded as illustrative and not limiting.

EXAMPLES

Example 1: Effect of ADPIF/PATAS Peptide on Glucose Absorption in Primary Human Mature Adipocyte Human primary preadipocyte were cultured in a 96-well plate and differentiated in mature human adipocytes. After 3 weeks of culture post adipogenesis, the adipocytes were incubated in culture medium without insulin for 2 hours. Following these 2 hours of insulin fasting, the media were changed back wither either medium without insulin (−INS) or medium with insulin (+INS) or medium with ADPIF (PATAS) for 30 minutes together with 2-DG, a glucose analogue used to determine glucose uptake in the Abcam kit. Following the manufacturer's protocol, we then measured the glucose uptake in 8 wells per condition and calculated the mean that was then plotted in the histogram with the standard error of the mean for the error bars shown in FIG. 1 FIG. 4.

Figure 5A:
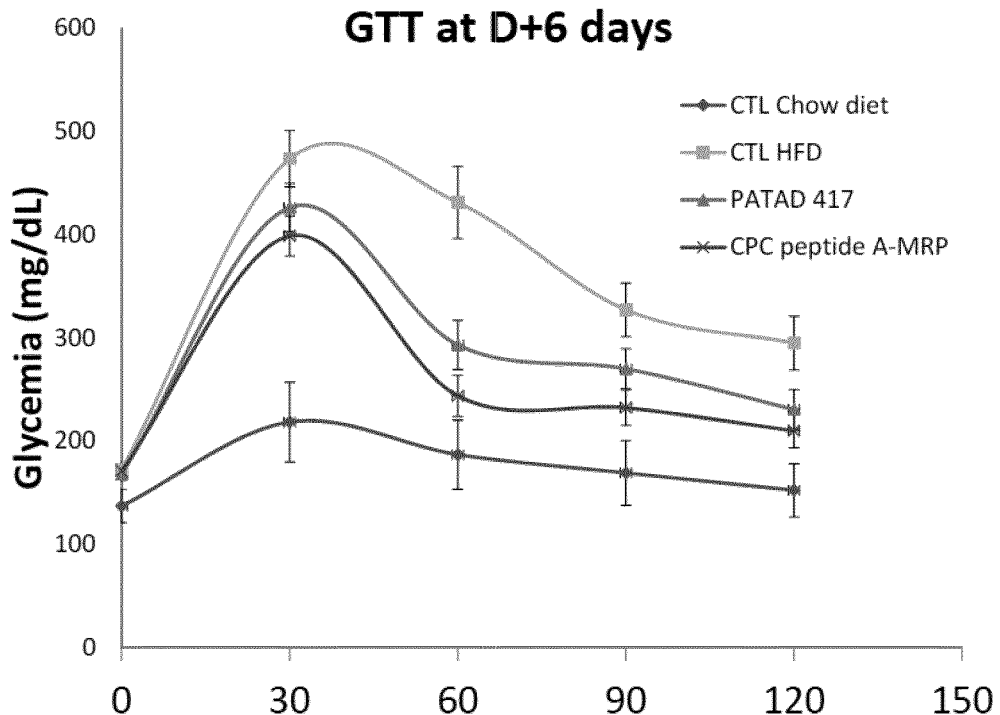
FIGS. 5A-5B. ADPIF peptide is more active than PATAD peptide in improving glucose intolerance in mice.
Figure 5B:
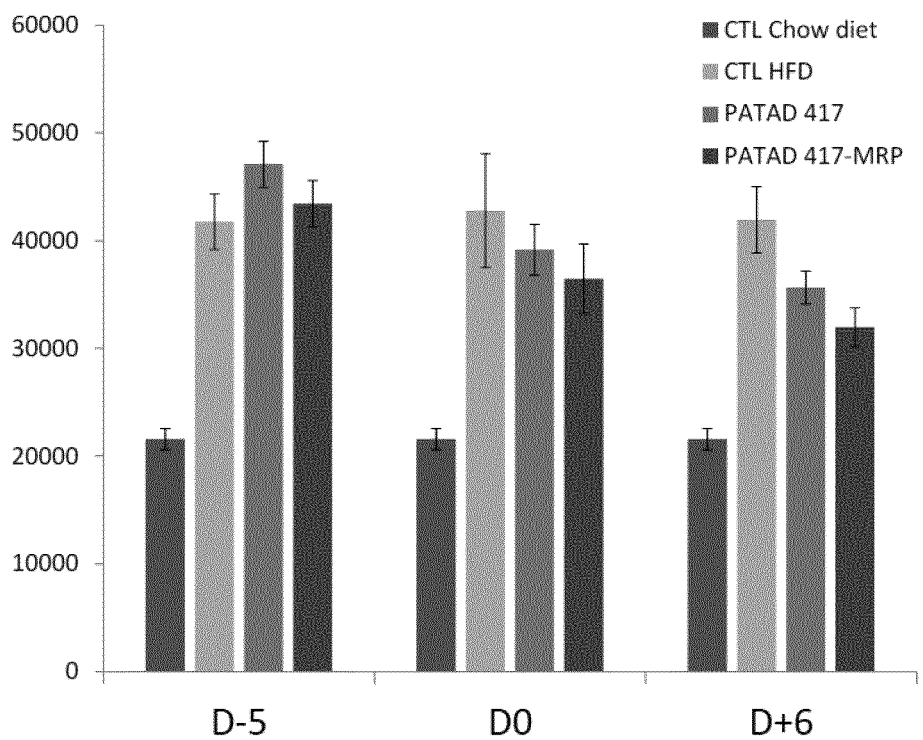

Example 2: ADPIF/PATAS Peptide is More Active than PATAD Peptide in Preventing Hyperglycemia Mice were injected with a single dose (25 micrograms per mouse) of either scramble peptide or PATAD or ADPIF/PATAS. These are results obtained from series of glucose tolerance test (ipGTT) in DIO glucose intolerant male mice (FIGS. 5A and B).

Figure 3:
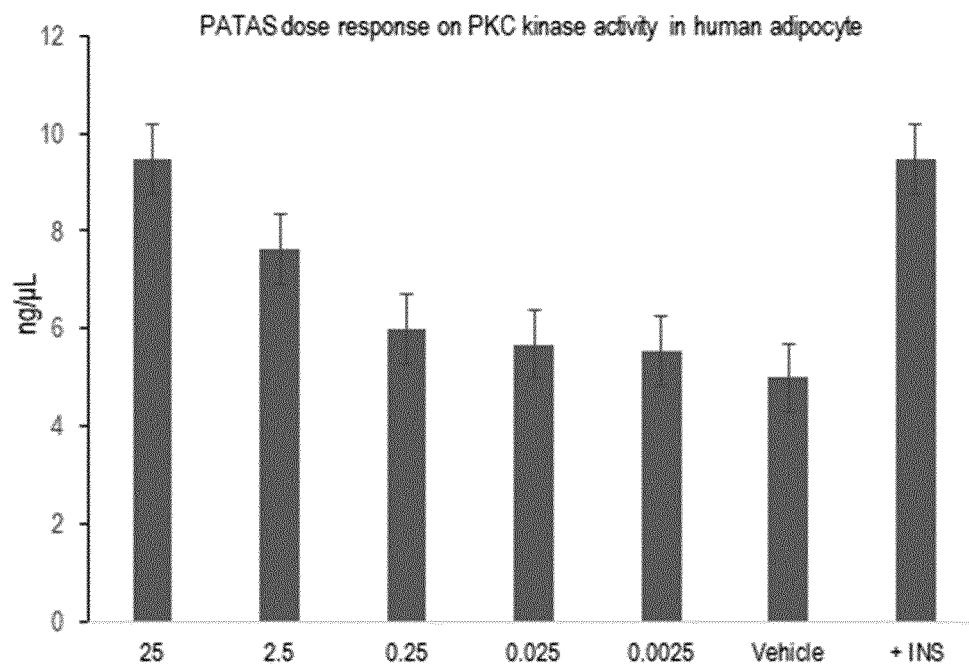
FIG. 3. PATAS in vitro dose response to trigger PKC activity in the human adipocytes. PATAS in vitro dose response to trigger PKC activity in the human adipocytes after a 30 minutes incubation of human primary adipocyte with PATAS added to the culture medium. n=5 per group and PATAS quantities are expressed as µg per well.

Example 3: ADPIF/PATAS Peptide Increases PKC Kinase Activity in Human Adipocyte with a Dose Response Effect As shown in FIG. 3, we can observe an increasing PKC activity with increasing ADPIF/PATAS quantity to reach similar levels of PKC activity at 25 ug of PATAS per well compared with Insulin.

Two other peptides from PKC alpha, namely ECTMVEKKVLALL (SEQ ID NO: 50) and SVEWWAYGLLYEMLA (SEQ ID NO: 51) have also been tested for their effect on PKC kinase activity. As shown in FIG. 1, both peptides are able to increase PKC kinase activity in human adipocyte.

Figure 2:
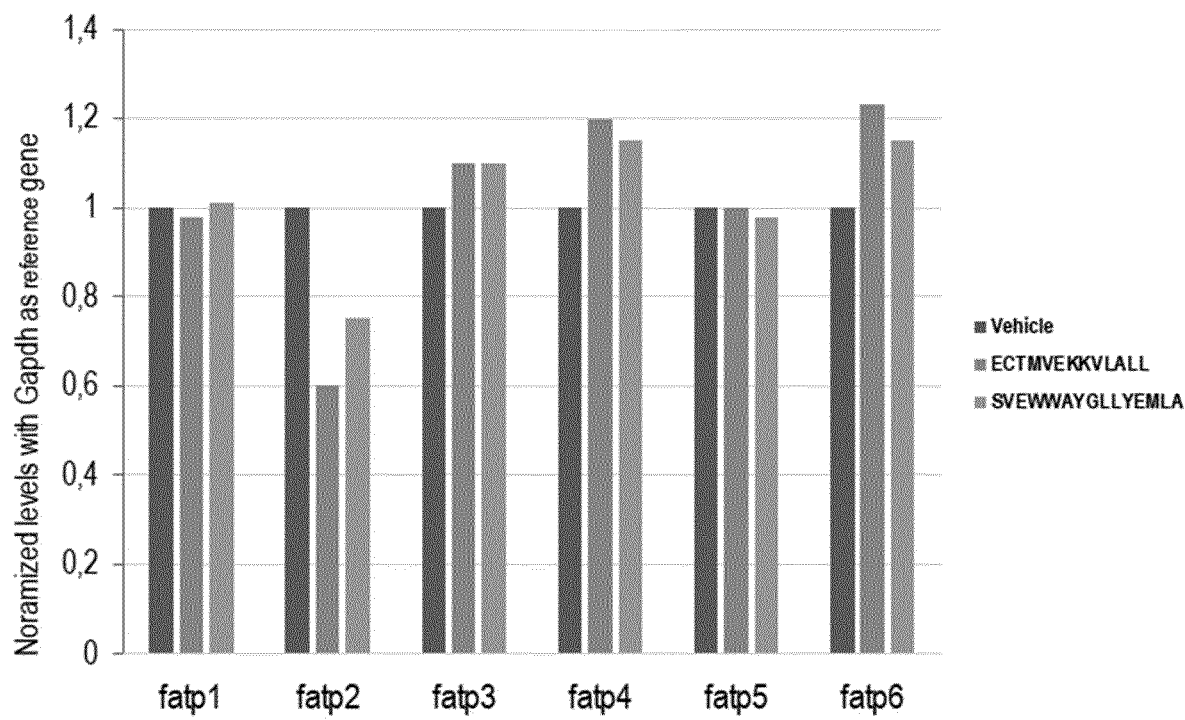
FIG. 2. FATP isoform expression level of human adipocytes treated with the peptides derived from the human alpha PKC. Following 48 hours of incubation with the different peptides derived from alpha PKC (namely ECTMVEKKVLALL (SEQ ID NO: 50) and SVEWWAYGLLYEMLA (SEQ ID NO: 51)) expression levels of the six isoforms of FATP were measured by real-time PCR. Normalized expression levels for the six FATP isoforms (Fatp1-6) in human adipocyte. GAPDH was used as reference gene.

In addition, the two peptides on the expression of FATP1-6 have been determined and both peptides decrease the expression of FATP2 in adipocytes (FIG. 2).

Example 4: Effect of ADPIF/PATAS Peptide in an Established Diabetic Mice Model (db/db; BKS Male Mice)

Figure 6A:
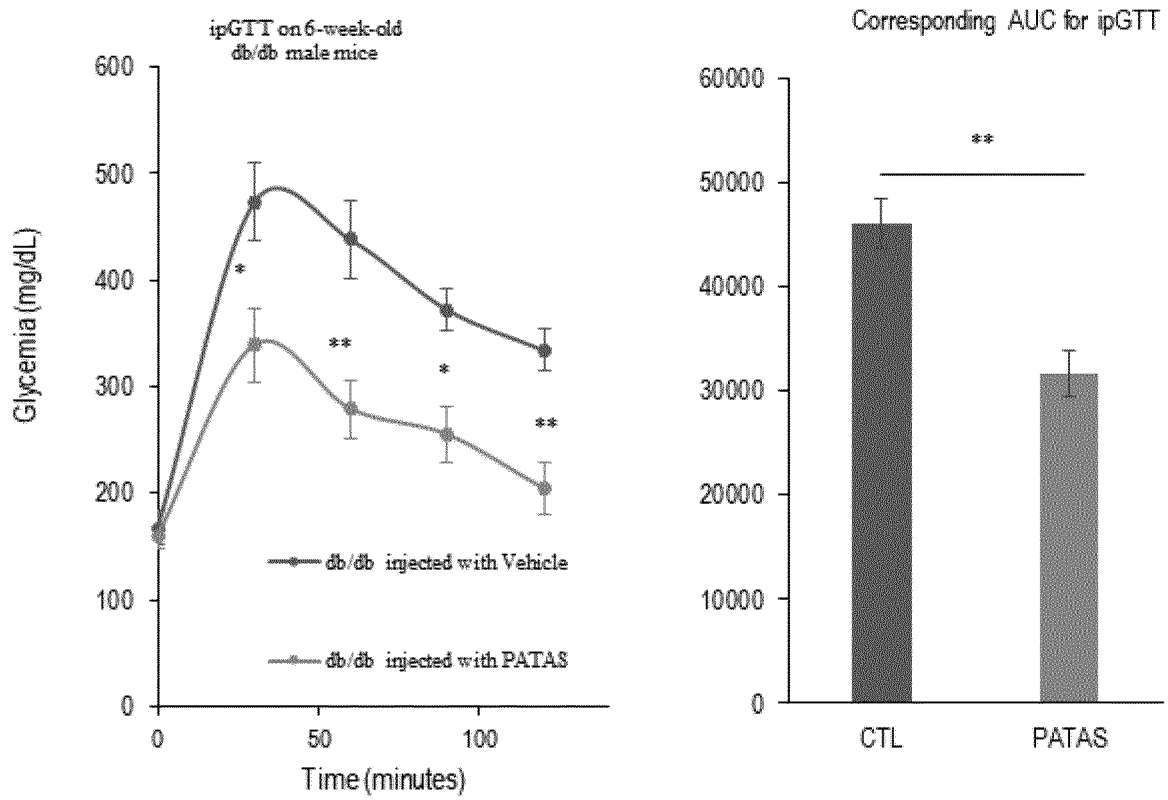
FIGS. 6A-6B. PATAS bears anti-diabetic in established diseases mouse model (db/db; BKS from Jax lab) associated with reduction of FATP2 expression levels in the adipose tissue.

As shown in FIG. 6A, the ADPIF/PATAS peptide is able to prevent hyperglycemia.

Figure 6B:
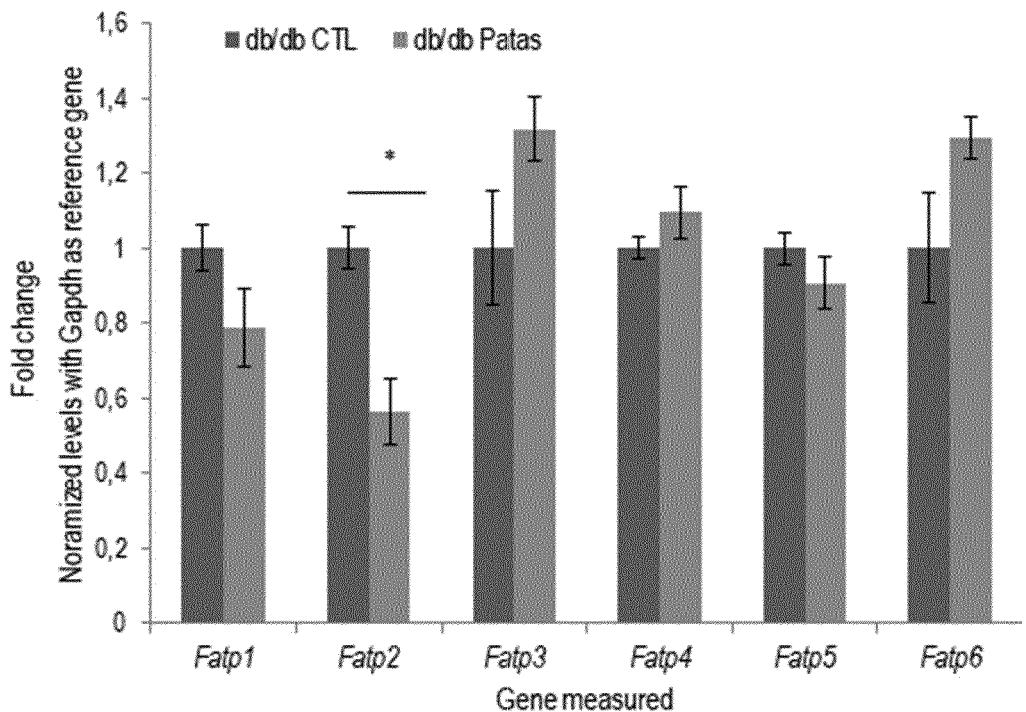
Figure 7A:
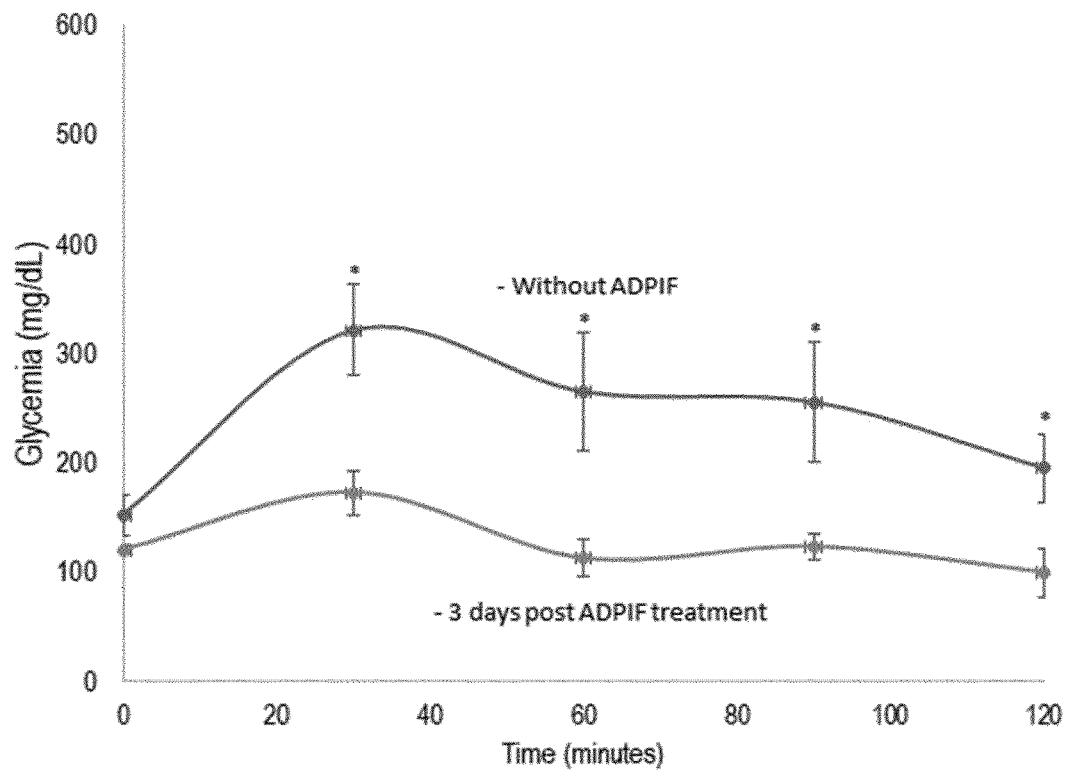
FIGS. 7A-7B. PATAS is effective in improving glucose intolerance in a genetic mouse model for a rare disease associated with obesity and type 2 diabetes, the Bardet Biedl syndrome (BBS). BBS mice were on chow diet fed ad libitum. n=4 mice with a cross-over experimental set-up with ipGTT performed before injection and 3 days post-injection. Knockout mouse model for the BBS10 gene (Bbs10$^{-/-}$) were generated and spontaneously became obese as described in literature. At 4 months of age, we performed an intraperitoneal glucose tolerance test (ipGTT) on the Bbs10$^{-/-}$ before administering PATAS and found that the Bbs10$^{-/-}$ mice were glucose intolerant (FIG. 7A) with a corresponding area under the curve (AUC) of ~30000 mg/dL·min (FIG. 7B). The same mice received 2 mg/kg of body weight of PATAS in the subcutaneous adipose tissue and 3 days later, we performed an ipGTT and found that the Bbs10$^{-/-}$ mice presented improved glucose tolerance (FIG. 7A) corresponding to a drop of the AUC to ~16000 mg/dL·min (FIG. 7B).
Figure 7B:
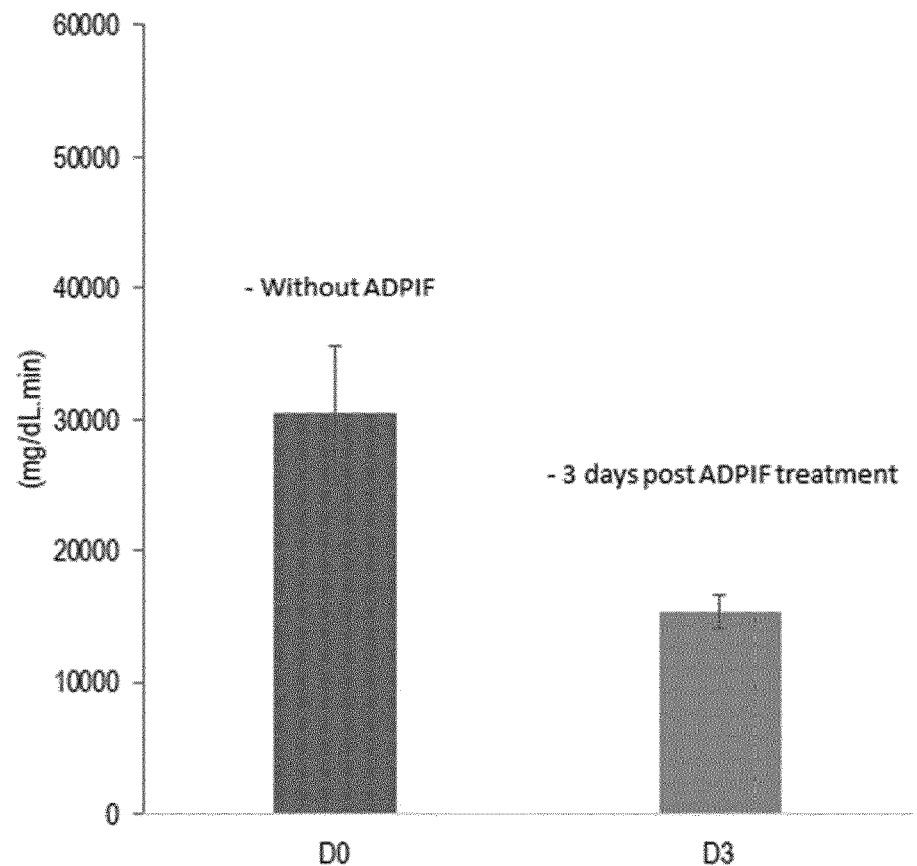

In addition, the effect of the ADPIF/PATAS peptide on the expression of FATP1-6 in adipocytes has been determined in this model. The ADPIF/PATAS peptide is able to decrease the expression of FATP2 (FIG. 6B).

PATAS/ADPIF's activity was tested in db/db on the BKS genetic background, diabetic mouse models. Six-week-old mice on chow diet either received a subcutaneous saline vehicle injection or a 2 mg/kg of body weight of PATAS injection and four days later, the ipGTT showed significant improvement of the glucose intolerance in response to PATAS/ADPIF administration (FIG. 6A). The mice received a weekly injection of PATAS/ADPIF or vehicle for another 3 weeks followed by another 4 weeks without any treatment while being constantly monitored. The db/db mice were then euthanized and the fatty acid transport protein isoforms (Fatps) expression levels in the adipose tissue were measured showing a specific and significant drop in Fatp2 expression levels for the PATAS-treated mice (FIG. 6B) compared to control mice.

Example 5: Effect of ADPIF/PATAS Peptide in a Bardet Biedl Syndrome (BBS) Model Knockout mouse model for the BBS10 gene (Bbs10$^{-/-}$) were generated and spontaneously became obese as described in literature. At 4 months of age, we performed an intraperitoneal glucose tolerance test (ipGTT) on the Bbs10$^{-/-}$ before administering PATAS/ADPIF and found that the Bbs10$^{-/-}$ mice were glucose intolerant (FIG. 7) with a corresponding area under the curve (AUC) of ~30000 mg/dL·min. The same mice received 2 mg/kg of body weight of PATAS in the subcutaneous adipose tissue and 3 days later, we performed an ipGTT and found that the Bbs10$^{-/-}$ mice presented improved glucose tolerance (FIG. 7) corresponding to a drop of the AUC to ~16000 mg/dL·min.

Figure 8:
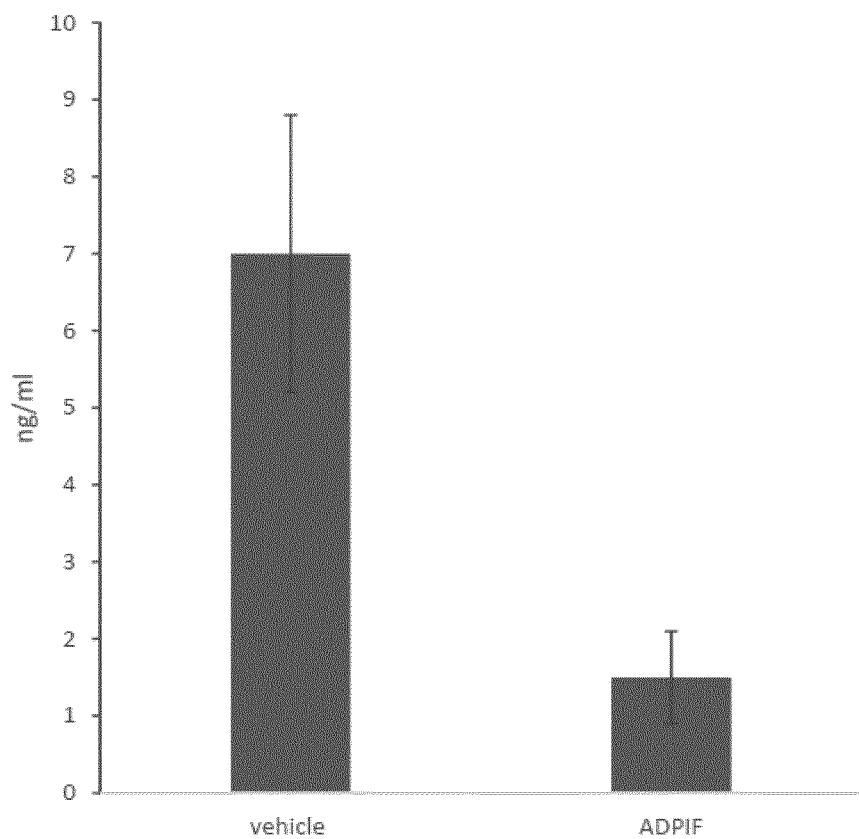
FIG. 8. Effect of ADPIF on glycated albumin in plasma in the STAM mice model. Plasma of the treated mice from the Japanese STAMT model were used to measure circulating glycated albumin levels using a commercially available kit. The results are presented in this figure as the mean value of 6 mice per group presented with the standard error of the mean for the error bars. Following the 5 weekly injections of ADPIF in the corresponding mice, we measured a significant drop in glycated albumin levels compared to the vehicle injected mouse group.

Example 6: ADPIF/PATAS is Effective in Decreasing Glycated Albumin in the STAMt Mouse Model after 5 Weeks of a Weekly Injection of 25 ug of ADPIF/PATAS Per Mouse Glycated albumin is a well-recognized and robust parameter to determine episodes of hyperglycemia in vivo. We therefore used the plasma from the STAMT mice that were treated for 5 weeks with weekly ADPIF/PATAS's injections at 25 ug each compared to control groups which were injected with saline. A significant drop in glycated albumin was measured in ADPIF/PATAS treated mice demonstrating that ADPIF/PATAS was able to improve hyperglyceamia (FIG. 8).

Materials & Methods

Peptide Sequences, Synthesis and Solution Preparation

PATAD stapled peptide sequence: VE CTM-[2-(4-pentenyl) alanine]-EK RVL A-[2-(4-pentenyl) alanine]-L DKP PFL TQL HS (SEQ ID NO: 49)

ADPIF/PATAS Stapled peptide sequence: VECTTREKEVLASLDKAAFLTQLHS (SEQ ID NO: 32) wherein R and S carry the stapling, being preferably 2-(7-octenyl)arginine and 2-(4-pentenyl)serine, respectively.

ECTMVEKKVLALL (SEQ ID NO 50) with M and A carrying the stapling.

SVEWWAYGLLYEMLA (SEQ ID NO 51) with A and M carrying the stapling.

The stapled peptides were used with a 95% purity.

All peptides were dissolved and diluted in sterile saline solution

Glucose Uptake Assay in Human Mature Adipocytes

Human white visceral preadipocytes (Catalog #: C-12732; PromoCell) were purchased. The preadipocytes were seeded according to manufacturer's protocol and cultured in the Preadipocyte growth medium (Catalog #: C-27410; PromoCell) to confluence. Adipogenic differentiation was induced by changing the medium to the Preadipocyte Differentiation Medium (Catalog #: C-27436; PromoCell) for 2 days. After the differentiation phase, the medium was finally changed to the Adipocyte Nutrition medium (Catalog #: C-27438; PromoCell). For the culture without insulin, Adipocyte Basal Medium (Catalog #: C-2431; PromoCell) without insulin was complemented with 5 g/L of deoxyglucose, 8 µg/mL d-Biotin, 400 ng/mL Dexamethasone. 3 weeks post adipogenic differentiation, the cultured mature adipocytes were cultured for 2 hours without insulin. Following these 2 hours, the culture medium was changed with fresh culture medium containing a glucose analogue (2-DG) either without insulin (−INS), or with insulin (+INS) or without insulin+2.5 µL of the tested peptide at a concentration of 10 µg/µL in a total final volume of 200 µL. After 30 minutes incubation, the cells were processed as indicated in the standard protocol from the commercially available kit of Glucose Uptake assay from Abcam: Glucose Uptake Assay Kit (Colorimetric) (Catalog #: ab136955).

For PKC kinase activity tests, we used ready to use mature primary human adipocytes originating from omental adipose tissue were purchased from Zenbio in either a 96-well or a 6-well plate format (Catalog #: OA-1096-3 or OA-1006-3). The PKC kinase activity Assay kit (Catalog #: 139437) and procedures were used according to manufacturer's protocol.

In Vivo Mouse Studies

For the obese mouse model with overt type 2 diabetes mouse, the BKS (D)-Leprdb/J, Stock No: 010803 (were purchased from the Jax Labs. Bbs10 knockout mice were generated by Institute Mouse Clinic (ICS) in Strasbourg and have been previously described in literature. All mice were on a C57/BL6 genetic background. All animals were housed in a temperature and humidity-controlled facility, with a 12 h-light/12 h-dark cycle. The BKS (D)-Leprdb/J mice were fed with chow diet (LM-485; Harlan Teklad Premier Laboratory Diets) whereas the Bbs knockout mice were fed with high fat/glucose diet and tap water ad libitum. For ipGTT and ipITT, mice were fasted for 6 hours before start of experiment. Insulin 0.75 U/kg was injected i.v. via the tail vein. Blood glucose and samples were collected from the tail. Mice were sacrificed by cervical dislocation.

For the non-obese STAM mouse model study, C57BL/6 mice (14-day-pregnant female) were obtained from Japan SLC, Inc. (Japan). All animals used in the study were housed and cared for in accordance with the Japanese Pharmacological Society Guidelines for Animal Use. The animals were maintained in a SPF facility under controlled conditions of temperature (23±2° C.), humidity (45±10%), lighting (12-hour artificial light and dark cycles; light from 8:00 to 20:00) and air exchange. The animals were housed in TPX cages (CLEA Japan) with a maximum of 3 mice per cage. Sterilized Paper-Clean (Japan SLC) was used for bedding and replaced once a week. Sterilized solid 60% HFD was provided ad libitum, being placed in a metal lid on the top of the cage. Pure water was provided ad libitum from a water bottle equipped with a rubber stopper and a sipper tube. Water bottles were replaced once a week, cleaned, and sterilized in an autoclave and reused.

Mice were identified by ear punch. Each cage was labeled with a specific identification code. NASH was induced in 12 male mice by a single subcutaneous injection of 200 µg streptozotocin (STZ, Sigma-Aldrich, USA) solution 2 days after birth and feeding with high fat diet (HFD, 57 kcal % fat, Cat #HFD32, CLEA Japan, Inc., Japan) after 4 weeks of age.

Dosage Regimen of the Peptides for the BKS (D)-Leprdb/J, Stock No: 010803 and the Bbs10 Knockout Mice At day 0: all mice were fasted for 4 hours in the morning. At 1:00 p.m., control mice received one injection of (body weight in grams)×10 milliliters of 22% glucose solution (retroperitoneal fat/subcutaneous injection). Treated mice were injected with either 25 ug (2.5 uL of mother solution) of tested peptide dissolved in (body weight in grams)×10 of the 22% glucose solution. Blood glucose levels were measured from tail vein blood at every 30 minutes intervals and plotted to determine the effect of the different treatments on the area under the curve.

Dosage Regiment of the Peptides for the STAM Mouse Model.

The tested peptide was ADPIF/PATAS peptide as described above.

Route of Drug Administration

The peptide was administered subcutaneously in the adipose tissue in a volume of 100 mL per mouse.

Experimental Design and Treatment

Study Groups

Group 1: ADPIF/PATAS Peptide

Six NASH mice were subcutaneously in the adipose tissue administered vehicle supplemented with ADPIF/PATAS peptide at a dose of 25 mg per mouse once weekly from 4 to 9 weeks of age.

Group 2: Vehicle

Six NASH mice were subcutaneously in the adipose tissue administered vehicle [DMSO in saline] in a volume of 100 mL per mouse once weekly from 4 to 9 weeks of age. The table below summarizes the treatment schedule:

| Group | No. mice | Mice | Test substance | Dose (μg per mouse) | Volume (μL per mouse) | Regimen | Sacrifice (wks) |
|---|---|---|---|---|---|---|---|
| 1 | 6 | STAM | Test peptide | 25 | 100 | SC, QW, 4-9 wks | 9 |
| 2 | 6 | STAM | Vehicle | — | 100 | SC, QW, 4-9 wks | 9 |

FATP Expression Levels

Total RNA was prepared from the different tissues and cells using a RiboPure™ kit (Catalog #: AM1924; Ambion) followed by a DNAse treatment with the TURBO DNA-free™ (Catalog #: AM 1907; Ambion). RNA integrity was assessed by gel electrophoresis and RNA concentration by Eppendorf Biophotometer Plus with the Hellma® Tray Cell (Catalog #: 105.810-uvs; Hellma). Reverse transcription of 1 μg total RNA to cDNA was performed using the BioRa-diScript™ cDNA synthesis kit (Catalog #: 170-8891; Bio-Rad). Real-time quantitative polymerase chain reaction amplification was performed in a BioRad CFX96 TM Real-Time System using the iQ™ SYBR® Green Supermix (Catalog #: 170-8886; BioRAd) and primer sets optimized for tested targets for SYBR Green-based real-time PCR for the real-time PCR. For human primers all qPCR primers used were purchased from Biorad validated MIQE primer sets.

| Gene name | Primer name | Primer sequence | PCR band size |
|---|---|---|---|
| Fatp1 | Mu_Slc27a1-RT-ex3F | TGCTTTGGTTTCTGGGACTT (SEQ ID NO 37) | 156 bp |
| | Mu_Slc27a1-RT-ex4R | GCTCTAGCCGAACACGAATC (SEQ ID NO 38) | |
| Fatp2 | Mu_Slc27a2-RT-ex4F | TGGACAAAGTAGACGGAGTGTC (SEQ ID NO 39) | 165 bp |
| | Mu_Slc27a2-RT-ex5R | TAGCAAGGCCTGTCCCATAC (SEQ ID NO 40) | |
| Fatp3 | Mu_Slc27a3-RT-ex9F | TGAGAACTTGCCACCGTATG (SEQ ID NO 41) | 171 bp |
| | Mu_Slc27a3-RT-ex10R | GGCAGGTAGGCCCCTATATC (SEQ ID NO 42) | |
| Fatp4 | Mu_Slc27a4-RT-ex2F | GTTTCATCCGGGTCTTCATC (SEQ ID NO 43) | 184 bp |
| | Mu_Slc27a4-RT-ex3R | GTGTCTGTGCCCTCGAAAAT (SEQ ID NO 44) | |
| Fatp5 | Mu_Slc27a5-RT-ex4F | AAGTTCTCTGCCTCCCGATT (SEQ ID NO 45) | 191 bp |
| | Mu_Slc27a5-RT-ex5R | CAAAGCGTTGCTGGAAGTTT (SEQ ID NO 46) | |
| Fatp6 | Mu_Slc27a6-RT-ex1F | TCGATTCCCTCCTACACTGC (SEQ ID NO 47) | 204 bp |
| | Mu_Slc27a6-RT-ex2R | TTGGTGGTACTGGCTCATCA (SEQ ID NO 48) | |

Measurement of Plasma Biochemistry

Sample Collection

The plasma samples were collected and stored at −80° C. for analysis. The plasma from these mice were then used to measure glycated albumin levels using a commercially available it from LS Bio: Mouse Glycated Albumin ELISA Kit (Sandwich ELISA)—LS-F28697 in Strasbourg.

Statistical Tests

Statistical analyses were performed using Student's t-test on GraphPad Prism 6 (GraphPad Software Inc., USA). P values <0.05 were considered statistically significant. A trend or tendency was assumed when a one-tailed t-test returned P values <0.1. Results were expressed as mean±SD.

The invention claimed is:

1. A method of treating diabetes and associated disorders selected from the group consisting of type I diabetes, type II diabetes, insulin resistance, diabetic retinopathy, diabetic neuropathy, diabetic nephropathy, hyperglycemia, hyperinsulinaemia and Bardet Biedl syndrome comprising the administration of a peptide to a subject in need of treatment, wherein:
   the peptide does not simultaneously comprise methionine, proline and arginine residues;
   the peptide adopts a secondary structure which is a helix or an alpha helix;
   the peptide has a length from 12 to 60 amino acids; and
      wherein the peptide sequence comprises one of the following sequences:

(SEQ ID NO: 27)
   VECTXXEKXVLAX;

(SEQ ID NO: 28)
   VECTXXEKXVLAXLDKXXFLTQLHS;

wherein the residues which are bold and underlined X carry a stapling and is any amino acid derivative suitable for stapling; and
   wherein X is any amino acid except M, P and R.

2. The method according to claim 1, wherein the peptide has a length of at least 12 amino acids and less than 40 amino acids.

3. The method according to claim 1, wherein the peptide sequence comprises one of the following sequences:

(SEQ ID NO: 53)
   VECTTXEKEVLAXLDKAAFLTQHS; or (SEQ ID NO: 54)
   VECTTXEKEVLAXLDKAAF;

wherein the residues which are bold and underlined X carry the stapling and is any amino acid derivative suitable for stapling; and
   wherein X is any amino acid except M, P and R.

4. The method according to claim 3, wherein X is an amino acid favorable to an α-helix secondary structure, or an amino acid selected from the group consisting of A, D, N, C, G, Q, E, H, L, K, F, S, W and Y.

5. The method according to claim 3, wherein the first bold and underlined X is 2-(7-octenyl) arginine and the second bold and underlined X is 2-(4-pentenyl) serine, respectively, and said first and second X carry the stapling.

6. The method according to claim 1, wherein the peptide sequence comprises:

(SEQ ID NO: 53)
   VECTTXEKEVLAXLDKAAFLTQLHS, wherein the first bold and underlined X is 2-(7-octenyl) arginine and the second bold and underlined X is 2-(4-pentenyl) serine, and said first and second X carry the stapling.

7. The method according to claim 1, wherein the peptide is used in combination with one or more additional active drugs selected from the group consisting of an anti-diabetic drug, a hypolipidemic agent, an anti-obesity agent, an anti-hypertensive agent, an anti-steatotic drug, an anti-inflammatory agent, and an agonist of peroxisome proliferator-activator receptors.

8. The method according to claim 2, wherein the peptide has a length of at least 12 amino acids and less than 25 amino acids.

9. The method according to claim 2, wherein the peptide has a length of at least 12 amino acids and less than 30 amino acids.

10. The method according to claim 3, wherein the peptide sequence consists of one of the following sequences:

(SEQ ID NO: 27)
   VECTXXEKXVLAX;

(SEQ ID NO: 28)
   VECTXXEKXVLAXLDKXXFLTQLHS;

(SEQ ID NO: 53)
   VECTTXEKEVLAXLDKAAFLTQHS; or (SEQ ID NO: 54)
   VECTTXEKEVLAXLDKAAF;

wherein the residues which are bold and underlined X carry the stapling and is any amino acid derivative suitable for stapling; and
   wherein X is any amino acid except M, P and R.

* * * * *

UNITED STATES PATENT AND TRADEMARK OFFICE
CERTIFICATE OF CORRECTION

PATENT NO. : 12,303,556 B2
APPLICATION NO. : 17/415796
DATED : May 20, 2025
INVENTOR(S) : Vincent Marion It is certified that error appears in the above-identified patent and that said Letters Patent is hereby corrected as shown below:

In the Specification

Column 2,
Line 14, "PKCa" should read --PKCα--.
Line 35, "of α" should read --of a--.
Line 37, "of α" should read --of a--.

Column 5,
Line 61, "bold and underlined X" should read --bold and underlined X--.

Column 6,
Line 16, "wherein R and S" should read --wherein R and S--.

Column 7,
Line 33, "T=Omin" should read --T=0min--.

Column 8,
Line 9, "PKCa" should read --PKCα--.

Column 11,
Line 35, "of α" should read --of a--.
Line 39, "of α" should read --of a--.
Line 40, "of α" should read --of a--.

Column 12,
Line 19, "of α" should read --of a--.
Line 29, "of α" should read --of a--.

Signed and Sealed this
Third Day of February, 2026

John A. Squires
*Director of the United States Patent and Trademark Office*

CERTIFICATE OF CORRECTION (continued)
U.S. Pat. No. 12,303,556 B2

Line 31, "of α" should read --of a--.
Line 32, "of α" should read --of a--.
Line 34, "of α" should read --of a--.
Line 43, "of α" should read --of a--.
Line 48, "of α" should read --of a--.

<u>Column 19,</u>
Line 55, "bold and underlined X" should read --bold and underlined X--.

<u>Column 20,</u>
Line 3, "first X" should read --first X--.
Line 5, "second X" should read --second X--.
Line 18, "wherein R and S" should read --wherein R and S--.

<u>Column 21,</u>
Line 36, "014975" should read --O14975--.

<u>Column 22,</u>
Line 8, "of α" should read --of a--.

Figure 4:
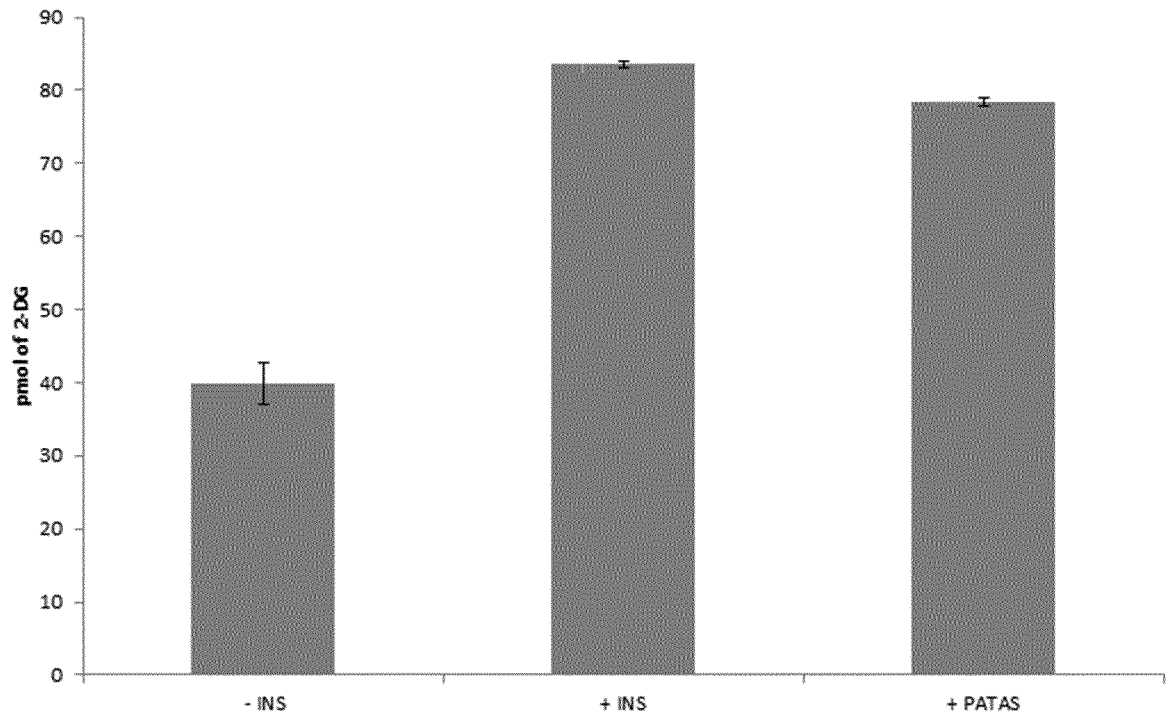
FIG. 4: Glucose uptake in human primary mature adipocyte. N=8 per group. ADPIF peptide is as effective as Insulin to trigger glucose absorption in primary human mature adipocytes.

<u>Column 28,</u>
Lines 2-3, "shown in FIG. 1 and FIG. 4" should read --shown in FIG. 4--.

<u>Column 29,</u>
Lines 29-30, "VECTTREKEVLASLDKAAFLTQLHS" should read
--VECTTREKEVLASLDKAAFLTQLHS--.
Line 31, "wherein R and S" should read --wherein R and S--.
Line 35, "ECTMVEKKVLALL (SEQ ID NO 50) with M and A" should read
--ECTMVEKKVLALL (SEQ ID NO 50) with M and A--.
Line 37, "SVEWWAYGLLYEMELA (SED ID NO 51) with A and M" should read
--SVEWWAYGLLYEMLA (SED ID NO 51) with A and M--.

In the Claims

<u>Column 63,</u>
Line 27, "VECTXXEKXVLAX" should read --VECTXXEKXVLAX--.
Line 30, "VECTXXEKXVLAXLDKXXFLTQLHS" should read
--VECTXXEKXVLAXLDKXXFLTQLHS--.
Line 31, "bold and underlined X" should read --bold and underlined X--.
Lines 38-47, "3. The method according to claim 1, wherein the peptide sequence comprises
one of the following sequences:
    VECTTXEKEVLAXLDKAAFLTQHS (SEQ ID NO: 53); or
    VECTTXEKEVLAXLDKAAF (SEQ ID NO: 54);

CERTIFICATE OF CORRECTION (continued)
U.S. Pat. No. 12,303,556 B2 wherein the residues which are bold and underlined X" should read
--3. The method according to claim 1, wherein the peptide sequence comprises one of the following sequences:

VECTXXEKXVLAX (SEQ ID NO: 27);
    VECTXXEKXVLAXLDKXXFLTQLHS (SEQ ID NO: 28);
    VECTTXEKEVLAXLDKAAFLTQHS (SEQ ID NO: 53); or
    VECTTXEKEVLAXLDKAAF (SEQ ID NO: 54);

wherein the residues which are bold and underlined X--.

Column 64,
Lines 9-12, "bold and underlined X is 2-(7-octenyl) arginine and the second bold and underlined X is 2-(4-pentenyl) serine, respectively, and said first and second X" should read
--bold and underlined X is 2-(7-octenyl)arginine and the second bold and underlined X is 2-(4-pentenyl)serine, respectively, and said first and second X--.
Line 17, "VECTTXEKEVLAXLDKAAFLTQLHS" should read
--VECTTXEKEVLAXLDKAAFLTQLHS--.
Lines 19-21, "bold and underlined X is 2-(7-octenyl) arginine and the second bold and underlined X is 2-(4-pentenyl) serine, and said first and second X" should read --bold and underlined X is 2-(7-octenyl)arginine and the second bold and underlined X is 2-(4-pentenyl)serine, and said first and second X--.
Line 49, "bold and underlined X" should read --bold and underlined X--.